(12) United States Patent
Alme et al.

(10) Patent No.: US 9,122,785 B2
(45) Date of Patent: Sep. 1, 2015

(54) DISPLAY OF SUPPLEMENTAL BOLUS IN RELATION TO PROGRAMMED DOSE

(75) Inventors: Sarah B. Alme, Blaine, MN (US); Touby A. Drew, Golden Valley, MN (US); Lance Beall, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 1360 days.

(21) Appl. No.: 12/691,513

(22) Filed: Jan. 21, 2010

(65) Prior Publication Data

US 2010/0185181 A1    Jul. 22, 2010

Related U.S. Application Data

(60) Provisional application No. 61/146,558, filed on Jan. 22, 2009.

(51) Int. Cl.
*G06T 11/20* (2006.01)
*G06F 19/00* (2011.01)
(Continued)

(52) U.S. Cl.
CPC ....... *G06F 19/3468* (2013.01); *A61M 5/14276* (2013.01); *A61B 19/56* (2013.01)

(58) Field of Classification Search
CPC .......... A61M 5/1723; A61M 5/31525; A61M 5/14276; A61M 5/16827; A61M 5/16877; A61M 5/16831; A61M 2005/14208; A61M 2005/3126; A61M 2005/1402; A61M 2205/502; A61M 2205/505; G06F 19/3468; G06F 19/3456; G06F 19/3487; G06F 19/3475; G06F 19/3481; G06F 19/3406; G06F 3/0484
USPC ........... 345/440, 440.2; 604/504, 64, 65, 151; 707/E17.009
See application file for complete search history.

(56) References Cited

U.S. PATENT DOCUMENTS 5,693,076 A    12/1997    Kaemmerer
5,722,999 A     3/1998    Snell
(Continued)

FOREIGN PATENT DOCUMENTS

EP    1 022 035 A1    7/2000
EP    1 681 069 A1    7/2006
(Continued)

OTHER PUBLICATIONS

Cao et al., "Design and simulation of an implantable medical drug delivery stems using microelectromechanical systems technology," Sensors and Actuators A 94 (2001), pp. 117-125.
(Continued)

*Primary Examiner* — Chante Harrison
(74) *Attorney, Agent, or Firm* — Shumaker & Sieffert, P.A.

(57) ABSTRACT

Techniques are described for displaying a representation of a supplemental bolus and a representation of programmed doses of a therapy schedule for an implantable fluid delivery device with a programmer device. In one example, a device includes a user interface to present a graphical representation of doses of fluid to be delivered to a patient via an implantable fluid delivery device and a processor that controls the user interface to simultaneously present a first graphical representation of a supplemental bolus to be delivered by the implantable fluid delivery device and a second graphical representation of programmed doses of a therapy schedule of the implantable fluid delivery device, wherein at least a portion of the programmed doses of the therapy schedule follows delivery of the supplemental bolus by the implantable fluid delivery device. A user of the device may determine whether the representations indicate an excessive dosage risk to the patient.

40 Claims, 22 Drawing Sheets

(51) Int. Cl.
*A61M 5/142* (2006.01)
*A61B 19/00* (2006.01)

(56) References Cited

U.S. PATENT DOCUMENTS

| | | | |
|---|---|---|---|
| 5,925,066 | A | 7/1999 | Kroll et al. |
| 6,007,493 | A | 12/1999 | Ericksen et al. |
| 6,442,433 | B1 | 8/2002 | Linberg |
| 6,675,044 | B2 | 1/2004 | Chen |
| 7,027,871 | B2 | 4/2006 | Burnes et al. |
| 7,047,065 | B2 | 5/2006 | Kalgren et al. |
| 7,072,725 | B2 | 7/2006 | Bristol et al. |
| 7,347,854 | B2 | 3/2008 | Shelton et al. |
| 7,366,570 | B2 | 4/2008 | Riff et al. |
| 2001/0012955 | A1 | 8/2001 | Goedeke et al. |
| 2001/0047194 | A1 | 11/2001 | Thompson et al. |
| 2002/0150872 | A1* | 10/2002 | Glenn et al. ............ 434/236 |
| 2002/0193679 | A1 | 12/2002 | Malave et al. |
| 2004/0088020 | A1 | 5/2004 | Condie et al. |
| 2004/0181204 | A1 | 9/2004 | Jasperson et al. |
| 2005/0043863 | A1 | 2/2005 | Ali et al. |
| 2005/0283210 | A1 | 12/2005 | Blischak et al. |
| 2006/0041222 | A1 | 2/2006 | Dewing et al. |
| 2006/0206066 | A1 | 9/2006 | Ferek-Petric |
| 2006/0272652 | A1 | 12/2006 | Stocker et al. |
| 2008/0033402 | A1 | 2/2008 | Blomquist |
| 2008/0177254 | A1 | 7/2008 | Shelton et al. |
| 2008/0249470 | A1 | 10/2008 | Malave et al. |
| 2008/0286330 | A1 | 11/2008 | Shafer et al. |
| 2009/0093756 | A1 | 4/2009 | Minaie et al. |
| 2010/0010646 | A1 | 1/2010 | Drew et al. |
| 2010/0064243 | A1 | 3/2010 | Buck et al. |
| 2011/0253586 | A1 | 10/2011 | Metry et al. |
| 2011/0264071 | A1* | 10/2011 | Braig et al. ............ 604/504 |
| 2012/0209241 | A1 | 8/2012 | Drew |
| 2012/0265126 | A1* | 10/2012 | Estes ....................... 604/66 |
| 2013/0274709 | A1* | 10/2013 | Shelton et al. ........... 604/507 |
| 2014/0032549 | A1* | 1/2014 | McDaniel et al. ..... 707/E17.009 |

FOREIGN PATENT DOCUMENTS

| | | |
|---|---|---|
| EP | 1845466 A2 | 10/2007 |
| WO | WO 03/099355 A2 | 12/2003 |
| WO | WO 2005/009514 A2 | 2/2005 |
| WO | WO 2005/107419 A2 | 11/2005 |
| WO | WO 2009/005957 A1 | 1/2009 |

OTHER PUBLICATIONS

Office action for U.S. Appl. No. 12/691,574, mailed Sep. 17, 2012, 11 pages.
International Search Report and Written Opinion of international application No. PCT/US20101021659, dated Nov. 16, 2010, 11 pp.
Patent Application entitled, "User Interface Indicating Fluid Location for an Implantable Fluid Delivery Device," U.S. Appl. No. 12/691,574, filed Jan. 21, 2010.
Patent Application entitled, "User Interface That Displays Pending and Selected Programming for an Implantable Medical Device," U.S. Appl. No. 12/691,592, filed Jan. 21, 2010.
Patent Application entitled, "Management of Session History Data for Implantable Fluid Delivery Device," U.S. Appl. No. 12/730,751, filed Mar. 24, 2010.
SynchroMed® II & SynchroMed® EL, Medtronic Reference Card, Bridge Bolus Calculation, Jan. 2008, 2 pages.
SynchroMed® II & SynchroMed® EL, Medtronic Reference Card, Catheter Revision Priming Volume Calculation, Jan. 2008, 2 pages.
SynchroMed® II & SynchroMed® EL, Medtronic Reference Card, Full Catheter Replacement Priming vol. Calculation, Jan. 2008, 2 pages.
SynchroMed® II & SynchroMed® EL, Medtronic Reference Card, Pump Replacement Priming Volume Calculation, Jan. 2008, 2 pages.
SynchroMed® 11, Programmable Infusion System Clinical Reference Guide, Intrathecal Baclofen for the Management of Severe Spasticity, 2007, 56 pages.
SynchroMed® II, Programmable Infusion System Clinical Reference Guide, Intrathecal Morphine for Pain Management, 2007, 54 pages.
SynchroMed® II, Programmable Infusion System Clinical Reference Guide, System Components, 2007, 60 pages.
SynchroMed® II, Programmable Infusion System Clinical Reference Guide, Therapy Maintenance, 2007, 79 pages.
Smart Card Alliance: News, Personal Health Cards Store Life-Saving Medical Information, Speed Up Hospital Administration: From Smart Card Alliance/CTST Conference, May 19, 2008, 2 pages.
Notification Concerning Transmittal of International Preliminary Report on Patentability for corresponding patent application No. PCT/US2010/021659, mailed Aug. 4, 2011, 6 pages.
Response to Office Action dated Sep. 17, 2012, from U.S. Appl. No. 12/691,574, filed Dec. 6, 2012, 16 pp.
Final Office Action dated Feb. 28, 2013, from U.S. Appl. No. 12/691,574, 12 pp.
Response to Final Office Action dated Feb. 28, 2013, from U.S. Appl. No. 12/691,574, filed Apr. 29, 2013, 16 pp.
Galanis et al., "Computer methods for automating preoperative dental implant planning: Implant positioning and size assignment," Computer Methods and Programs in Biomedicine 86, Apr. 2007, pp. 30-38.
Office Action from U.S. Appl. No. 12/691,574, dated Aug. 16, 2013, 11 pp.
Office Action from U.S. Appl. No. 12/691,592, dated Aug. 6, 2013, 17 pp.
Response to Office Action dated Aug. 6, 2013, from U.S. Appl. No. 12/691,592, filed Oct. 7, 2013, 15 pp.
Response to Office Action dated Aug. 16, 2013, from U.S. Appl. No. 12/691,574, filed Nov. 15, 2013, 16 pp.
Office Action for U.S. Appl. No. 12/691,592, dated Apr. 15, 2013, 15 pp.
Response to office action for U.S. Appl. No. 12/691,592, filed Jul. 15, 2013, 16 pages.
Response to Office Action dated Feb. 5, 2014, from U.S. Appl. No. 12/691,592, filed May 5, 2014, 15 pp.

* cited by examiner

FIG. 7

DISPLAY OF SUPPLEMENTAL BOLUS IN RELATION TO PROGRAMMED DOSE

This application claims the benefit of U.S. Provisional Application No. 61/146,558, filed Jan. 22, 2009, which is hereby incorporated by reference in its entirety.

TECHNICAL FIELD

This disclosure relates to programmers that control programming of implantable medical devices, such as implantable drug pumps.

BACKGROUND

A variety of medical devices are used for chronic, i.e., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician. The devices may be implantable medical devices that receive the program from a programmer controlled by the clinician.

Examples of such implantable medical devices include implantable fluid delivery devices, implantable neurostimulators, implantable cardioverters, implantable cardiac pacemakers, implantable defibrillators, cochlear implants, and others that now exist or may exist in the future. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device which can deliver a fluid medication to a patient at a selected site. A drug infusion device may be implanted at a location in the body of a patient and deliver a fluid medication through a catheter to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the IMD of a fluid delivered to the patient.

Programmable implantable medical devices are typically programmed using an external programming device, sometimes known as a controller or programmer, which can communicate with the implanted medical device through well known techniques such as wireless telemetry. An external controller, or programmer, can be used by a medical professional, for example, to change the therapeutic regimen by increasing or decreasing the amount of fluid medication delivered to the patient. Typically, a medical professional interfaces with the external controller or programmer to set various parameters associated with the implantable medical device and then transmits, or downloads, those parameters to the implanted medical device. The external device may also record other information important to the delivery of the therapy. Some information may be stored in the implantable medical device and/or the external programming device. Such information may include patient information, implanted device information such as model, volume, implant location, length of catheter or lead, and other information specific to different devices.

SUMMARY

In general, techniques are described for displaying both a graphical representation of a supplemental bolus to be administered by an implantable fluid delivery device, such as an implantable fluid delivery pump, and a graphical representation of a therapy schedule of the implantable fluid delivery device. A device for programming the implantable fluid delivery device receives a dosing program, which includes definitions of the supplemental bolus and the therapy schedule, to be administered by the implantable fluid delivery device. The dosing program may further include a definition of a priming bolus and/or a definition of a bridging phase of the implantable fluid delivery device. The device for programming the implantable fluid delivery sends, e.g., downloads, the dosing program to the implantable fluid delivery device, and the implantable fluid delivery device administers fluid, which may include one or more medications, to a patient in accordance with the dosing program.

In one example, a method includes displaying, with a device for programming an implantable fluid delivery device, a first graphical representation of a supplemental bolus to be delivered by the implantable fluid delivery device, and displaying, simultaneously with the first graphical representation, a second graphical representation of programmed doses of a therapy schedule to be delivered by the implantable fluid delivery device.

In another example, a programmer device includes a user interface comprising a display to present a graphical representation of doses of fluid to be delivered to a patient via an implantable fluid delivery device; and a processor that controls the user interface to simultaneously present on the display a first graphical representation of a supplemental bolus to be delivered by the implantable fluid delivery device and a second graphical representation of programmed doses of a therapy schedule of the implantable fluid delivery device, wherein at least a portion of the programmed doses of the therapy schedule follows delivery of the supplemental bolus by the implantable fluid delivery device.

In another example, a system includes an implantable fluid delivery device that delivers fluid to a patient according to a dosing program, comprising a computer-readable medium to store the dosing program and a telemetry module, and a programmer device comprising a user interface comprising a display to present a graphical representation of doses of fluid to be delivered to a patient via an implantable fluid delivery device, and a processor that controls the user interface to simultaneously present on the display a first graphical representation of a supplemental bolus to be delivered by the implantable fluid delivery device and a second graphical representation of programmed doses of a therapy schedule of the implantable fluid delivery device, wherein at least a portion of the doses of the therapy schedule follows delivery of the supplemental bolus by the implantable fluid delivery device.

In another example, a device includes means for displaying a first graphical representation of a supplemental bolus to be delivered by an implantable fluid delivery device, and means for displaying, simultaneously with the first graphical representation, a second graphical representation of programmed doses of a therapy schedule to be delivered by the implantable fluid delivery device.

In another example, a computer-readable medium, such as a computer-readable storage medium, contains instructions that cause a programmable processor to display first graphical representation of a supplemental bolus to be delivered by the implantable fluid delivery device; and display, simultaneously with the first graphical representation, a second graphical representation of programmed doses of a therapy schedule to be delivered by the implantable fluid delivery device.

The details of one or more examples are set forth in the accompanying drawings and the description below. Other features, objects, and advantages will be apparent from the description and drawings, and from the claims.

BRIEF DESCRIPTION OF DRAWINGS

FIG. 7 is a screenshot illustrating an example user interface screen presented by an external programmer for editing fluid delivery pump and catheter information.

DETAILED DESCRIPTION

Figure 1:
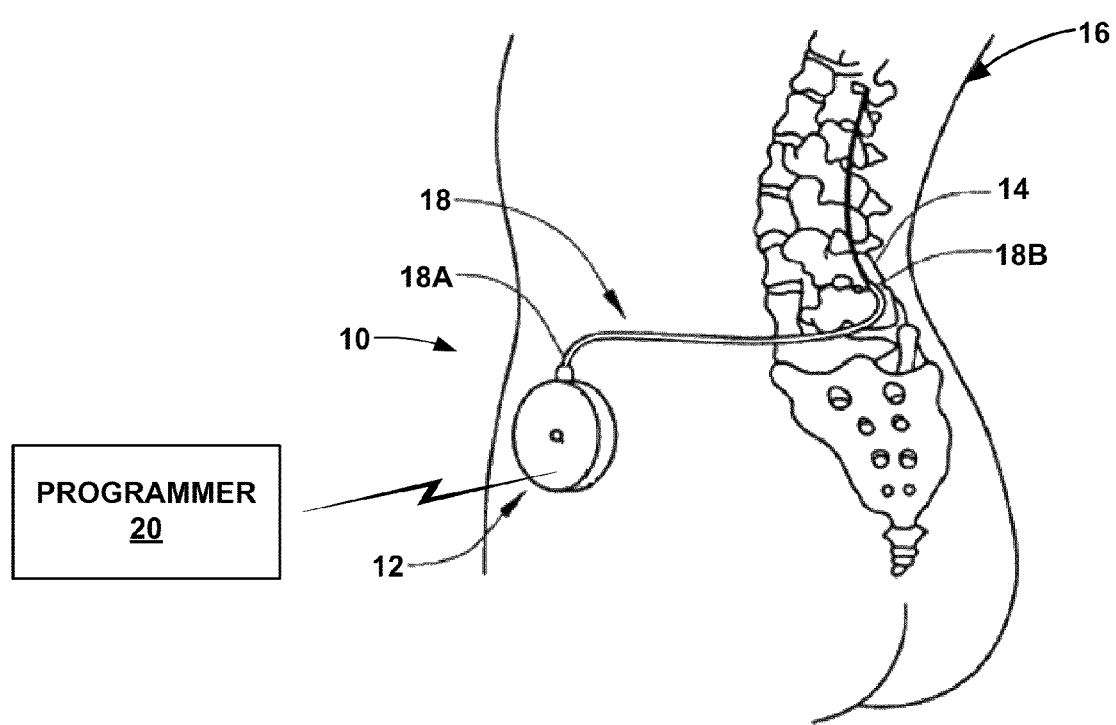
FIG. 1 is a conceptual diagram illustrating an example of a fluid delivery system, which includes an implantable medical device that is configured to deliver a therapeutic agent to a patient via a catheter.

Medical devices are useful for treating, managing or otherwise controlling various patient conditions or disorders, such as, but not limited to, pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices may be configured to deliver one or more therapeutic agents, alone or in combination with other therapies, such as electrical stimulation, to one or more target sites within a patient. For example, in some cases, a medical device may deliver insulin to a patient with diabetes. The medical device may be implanted in the patient for chronic therapy delivery (e.g., longer than a temporary, trial basis) or temporary delivery.

As used in this disclosure, the term dosing program generally refers to a program sent to an implantable fluid delivery device by a device for programming the implantable fluid delivery device to cause the implantable fluid delivery device to deliver fluid at a certain rate at a certain time. The dosing program may include, for example, definitions of a priming bolus, a bridging phase, a supplemental bolus, and a therapy schedule. A dosing program may include additional information, such as patient information, permissions for a user to add a supplemental bolus, historical therapy schedules, fluid or drug information, or other information. The term therapy schedule refers to a rate (which may be zero) at which to administer fluid, or a drug or drug combination within the fluid, at a specific time to a patient. In particular, the therapy schedule may define one or more programmed doses, which may be periodic or aperiodic, each dose including a dose rate and a time duration at which to deliver the dose. Dose rate generally refers to the amount of drug delivered over a period of time, and may change over the course of a therapy schedule such that a drug may be delivered at different rates at different times.

A priming bolus refers to a bolus delivered by the implantable fluid delivery device to move the fluid to the distal tip of the catheter, i.e., the tip of the catheter that is remote from the reservoir and internal tubing, if applicable. Once the fluid is primed to the distal tip of the catheter, the IMD is ready to deliver fluid to the patient from the distal tip, e.g., via one or more fluid outlets at or near the distal tip. The device delivers the priming bolus during a "priming phase" to prepare the device for delivery of fluid to the patient. An implantable fluid delivery device also may perform a "bridge" when a new fluid is inserted into a reservoir of the device while an old fluid is still present in the device, e.g., within internal tubing of the device and/or within a catheter connected to the device. The bridge is performed to define a rate at which to deliver the old fluid until the old fluid is completely delivered out of the catheter and to the patient such that the device contains only the new fluid. A supplemental bolus is a bolus administered to the patient outside of the therapy schedule. The terms independent bolus, one-time bolus, and therapeutic bolus may also be used in this disclosure to refer to a supplemental bolus. In particular, therapeutic bolus and supplemental bolus may be used generally interchangeably in this disclosure. In one example, the implantable fluid delivery device may administer a supplemental bolus before the implantable fluid delivery device begins administering doses of fluid according to the therapy schedule. In another example, the implantable fluid delivery device may administer a supplemental bolus during the therapy schedule, e.g., to override or supplement the therapy schedule in response to clinician instruction or patient request.

A patient may, under various circumstances, not have received a dose of the fluid for a period of time. For example, doctors may have replaced an old implantable fluid delivery device with a new fluid delivery device, flushed an implantable fluid delivery device that was implanted in the patient, modified the implantable fluid delivery device, refilled the implantable fluid delivery device, changed a fluid to be administered by the implantable fluid delivery device, or otherwise taken an action that stopped the implantable fluid delivery device from delivering fluid to the patient. The implantable fluid delivery device may also have malfunctioned, requiring repair or replacement of the device, thus preventing delivery of fluid to the patient.

In any case, a clinician or other user of a programmer device that interacts with the implantable fluid delivery device may decide to program a supplemental, therapeutic bolus to be administered by the implantable fluid delivery device after the implantable fluid delivery device has been reprogrammed by the programmer device. That is, the clinician may decide that a therapeutic bolus is necessary to quickly restore therapeutic efficacy to the patient after a period of time during which the patient may have been deprived of doses of the fluid. Under certain circumstances, the supplemental, therapeutic bolus may occur in close temporal proximity to a programmed dose delivered according to a therapy schedule that may commence upon reactivation of the normal operation of the pump. In these circumstances, the patient may face a risk of receiving an excessive dosage of a drug in the fluid. The programmer device may, in accordance with the techniques described in this disclosure, simultaneously display both a graphical representation of the supplemental, therapeutic bolus and a graphical representation of one or more programmed doses to be delivered according to the therapy schedule. Upon observing these graphical representations, the clinician may decide whether the graphical representations indicate a possibility of an excessive dosage for the patient. The clinician may therefore either proceed to program the implantable fluid delivery device with the dosing program, when there is no excessive dosage risk, proceed with the dosing program but monitor the patient to determine whether the patient presents symptoms of excessive dosage, modify the dosing program to avoid the risk of excessive dosage, or take other action based on the graphical representations provided by the programmer device.

FIG. 1 is a conceptual diagram illustrating an example of a therapy system 10, which includes implantable medical device (IMD) 12 configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. In one example, catheter 18 may comprise a plurality of catheter segments. In other examples, catheter 18 may be a unitary catheter. In the example of FIG. 1, the therapeutic agent is a therapeutic fluid. IMD 12 may be, for example, an implantable fluid delivery device that delivers therapeutic agents in fluid form to patient 16. In the example shown in FIG. 1, the target site is proximate to spinal cord 14 of patient 16. A proximal end 18A of catheter 18 is coupled to IMD 12, while a distal end 18B of catheter 18 is located proximate to the target site. Therapy system 10 also includes external programmer 20, which wirelessly communicates with IMD 12 as needed, such as to provide or retrieve therapy information or control aspects of therapy delivery (e.g., modify the therapy parameters, turn IMD 12 on or off, and so forth). While patient 16 is generally referred to as a human patient, other mammalian or non-mammalian patients are also contemplated.

Generally, IMD 12 has an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

Catheter 18 may be coupled to IMD 12 either directly or with the aid of a catheter extension (not shown in FIG. 1). In the example shown in FIG. 1, catheter 18 traverses from the implant site of IMD 12 to one or more target sites proximate to spine 14. Catheter 18 is positioned such that one or more fluid delivery outlets of catheter 18 are proximate to the one or more target tissue or nerve sites within patient 16. IMD 12 delivers a therapeutic agent to the one or more target tissue or nerve sites proximate to spinal cord 14 with the aid of catheter 18. For example, IMD 12 may be configured for intrathecal drug delivery into the intrathecal space or epidural space surrounding spinal cord 14. The intrathecal space is within the subarachnoid space of spinal cord 14, which is past the epidural space and dura mater and through the theca of spinal cord 14.

Therapy system 10 may be used, for example, to reduce pain experienced by patient 16. IMD 12 may deliver one or more therapeutic agents to patient 16 according to one or more dosing programs that set forth different therapy parameters, such as a therapy schedule specifying programmed doses, dose rates for the programmed dose, and specific times to deliver the programmed doses. In some examples, the therapeutic agent may be a liquid. The dosing programs may be may be a part of a program group for therapy, where the group includes a plurality of therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the type of therapeutic agent(s) delivered by IMD 12, a baseline orientation of at least a portion of IMD 12 relative to a reference point, therapy parameters of dosing programs stored within IMD 12 or within programmer 20, and any other information the clinician desires to program into IMD 12.

The clinician uses programmer 20 to program IMD 12 with one or more therapy programs that define the therapy delivered by IMD 12. During a programming session, the clinician may determine one or more dosing programs that may provide effective therapy to patient 16. Patient 16 may provide feedback to the clinician as to the efficacy of a specific program being evaluated or desired modifications to the dosing program. Once the clinician has identified one or more programs that may be beneficial to patient 16, patient 16 may continue the evaluation process and determine which dosing program best alleviates the condition of patient 16 or otherwise provides efficacious therapy to patient 16. The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the therapy program. Programmer 20 may assist the clinician in the creation/identification of therapy programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects. Program information specified by a user via programmer 20 may be used to control dosage amount, dosage rate, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 16 may be a location proximate to sacral nerves (e.g., the S2, S3, or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. As further examples, catheter 18 may be positioned to deliver a therapeutic agent to help manage peripheral neuropathy or post-operative pain mitigation, ilioinguinal nerve stimulation, intercostal nerve stimulation, gastric stimulation for the treatment of gastric motility disorders and/or obesity, muscle stimulation, for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent within the brain may help manage any number of disorders or diseases. Example disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents that IMD 12 may be configured to deliver include, but are not limited to, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics.

In accordance with the techniques described herein, programmer 20 may display representations of both a supplemental bolus, e.g., a therapeutic bolus, and programmed doses to be delivered according to a therapy schedule of the dosing program simultaneously, e.g., presenting graphical representations of both the therapeutic bolus and the programmed doses on a single graph. For example, programmer 20 may display a first graphical representation of a supplemental bolus to be delivered by the implantable fluid delivery device and display, simultaneously with the first graphical representation, a second graphical representation of programmed doses of a therapy schedule to be delivered by the implantable fluid delivery device. In this manner, the clinician may readily observe when both the supplemental bolus and the doses of the therapy schedule are to be delivered. The clinician may therefore determine, before causing programmer 20 to program IMD 12 with a dosing program, whether the programming of the supplemental, therapeutic bolus and/ or the therapy schedule should be altered. The clinician may further accept the programming or alter the programming as necessary before programming IMD 12.

Figure 2:
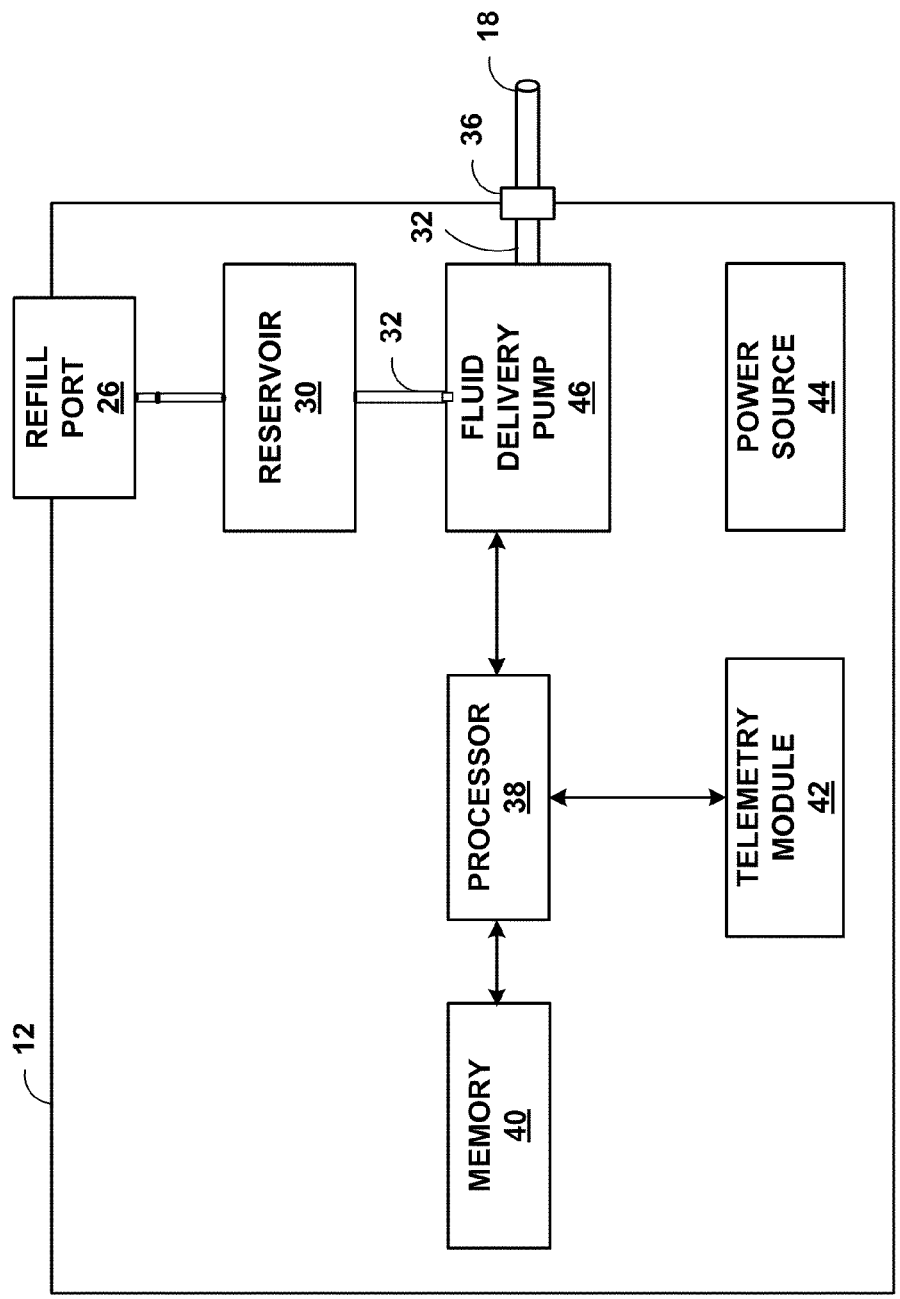
FIG. 2 is functional block diagram illustrating an example of an implantable fluid delivery device.

FIG. 2 is a functional block diagram illustrating components of an example of IMD 12, which includes refill port 26, reservoir 30, processor 38, memory 40, telemetry module 42, power source 44, fluid delivery pump 46, internal tubing 32, and catheter access port 36. Fluid delivery pump 46 may be a mechanism that delivers a therapeutic agent in some metered or other desired flow dosage to the therapy site within patient 16 from reservoir 30 via the catheter 18. Refill port 26 may comprise a self-sealing membrane to prevent loss of therapeutic agent delivered to reservoir 30 via refill port 26. After a delivery system, e.g., a hypodermic needle, penetrates the membrane of refill port 26, the membrane may seal shut when the needle is removed from refill port 26.

Internal tubing 32 is a segment of tubing that runs from reservoir 30, around or through fluid delivery pump 46, to catheter access port 36. In one example, fluid delivery pump 46 may be a squeeze pump that squeezes internal tubing 32 in a controlled manner, e.g., such as a peristaltic pump, to progressively move fluid from reservoir 30 to the distal end of catheter 18 and then into the patient according to parameters specified by a set of program information. Fluid delivery pump 46 may, in other examples, comprise an axial pump, a centrifugal pump, a pusher plate, a piston-driven pump, or other means for moving fluid through internal tubing 32 and catheter 18.

Processor 38 controls the operation of fluid delivery pump 46 with the aid of instructions associated with program information that is stored in memory 40. For example, the instructions may define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of the dosage rate at which the fluid is delivered. The therapy programs may also include other therapy parameters, such as the frequency of bolus delivery, the type of therapeutic agent delivered if IMD 12 is configured to deliver more than one type of therapeutic agent), and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, therapy programs, historical therapy programs, timing programs for delivery of fluid from reservoir 30 to catheter 18, and any other information regarding therapy of patient 16. A program may indicate the bolus size or flow rate of the drug, and processor 38 may accordingly deliver therapy. Memory 40 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 40 stores program instructions that, when executed by processor 38, cause IMD 12 and processor 38 to perform the functions attributed to them in this disclosure.

Telemetry module 42 in IMD 12, as well as telemetry modules in other devices described herein, such as programmer 20, may accomplish communication by RF communication techniques. In addition, telemetry module 42 may communicate with programmer 20 via proximal inductive interaction of IMD 12 with external programmer 20. Accordingly, telemetry module 42 may send information to external programmer 20 on a continuous basis, at periodic intervals, or upon request from the programmer. Processor 38 controls telemetry module 42 to send and receive information. Wireless telemetry may be accomplished by RF communication or proximal inductive interaction of IMD 12 with external programmer 20.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Figure 3:
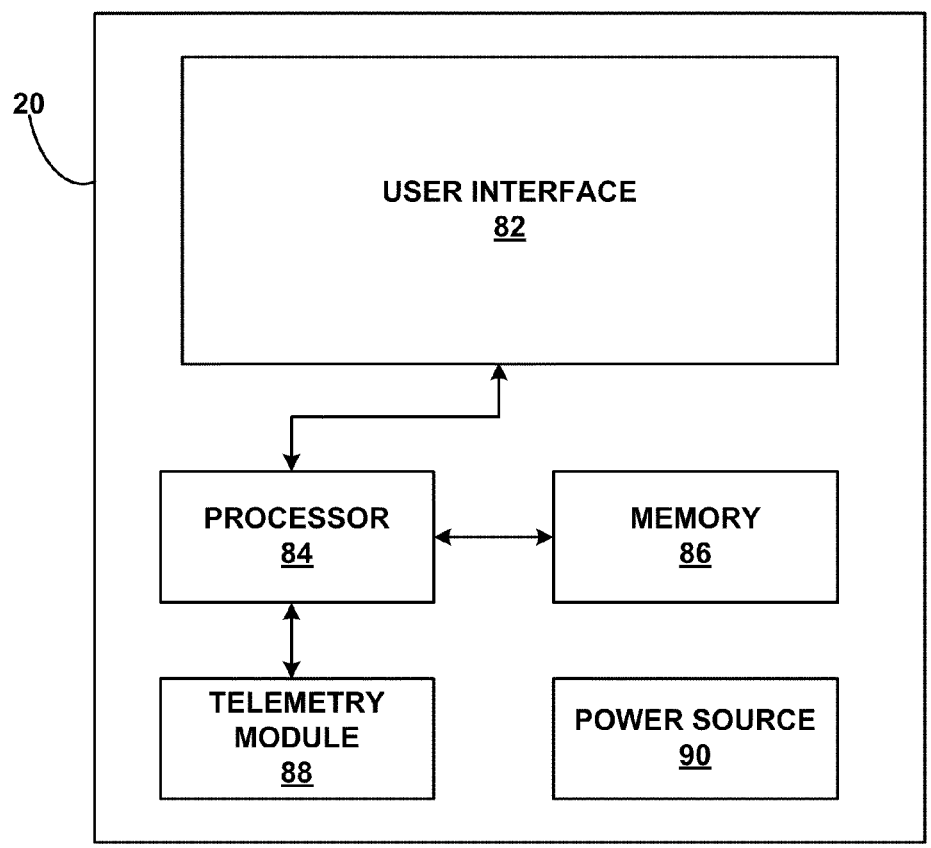
FIG. 3 is a functional block diagram illustrating example components of an external programmer for an implantable medical device.

FIG. 3 is a functional block diagram illustrating various components of an external programmer 20 for IMD 12. As shown in FIG. 3, external programmer 20 includes processor 84, memory 86, telemetry module 88, user interface 82, and power source 90. A clinician or patient 16 interacts with user interface 82 in order to manually change the parameters of a dosing program, change dosing programs within a group of programs, view therapy information, view historical therapy regimens, establish new therapy regimens, or otherwise communicate with IMD 12 or view programming information.

User interface 82 may include a screen and one or more input buttons, as discussed in greater detail below, that allow external programmer 20 to receive input from a user. Alternatively, user interface 82 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible indications of dosing program parameters or operational status, a display screen may suffice. For audible and/or tactile indications of dosing program parameters or operational status, programmer 20 may further include one or more audio speakers, voice synthesizer chips, piezoelectric buzzers, or the like.

Input buttons for user interface 82 may include a touch pad, increase and decrease buttons, emergency shut off button, and other buttons needed to control the therapy, as described above with regard to patient programmer 20. Processor 84 controls user interface 82, retrieves data from memory 86 and stores data within memory 86. Processor 84 also controls the transmission of data through telemetry module 88 to IMD 12. The transmitted data may include dosing program information specifying various drug delivery program parameters. Memory 86 may include operational instructions for processor 84 and data related to therapy for patient 16.

User interface 82 may be configured to present dosing program information to the user. User interface 82 enables a user to program IMD 12 in accordance with one or more dosing programs, e.g., programs that define a therapy schedule for delivering programmed doses of fluid, a priming bolus, a therapeutic bolus, a bridging process, or similar information. As discussed in greater detail below, a user such as a clinician, physician or other caregiver may input patient information, drug information, therapy delivery schedules, priming information, bridging information, drug/IMD implant location information, or other information to programmer 20 via user interface 82. In addition, user interface 82 may display dosing program information as graphical bar graphs or charts, numerical spread sheets, or in any other manner in which information may be displayed. Further, user interface 82 may present nominal or suggested therapy parameters that the user may accept via user interface 82. In this manner, user interface 82 may display a first graphical representation of a supplemental bolus to be delivered by the implantable fluid delivery device and display, simultaneously with the first graphical representation, a second graphical representation of programmed doses of a therapy schedule to be delivered by the implantable fluid delivery device.

User interface 82 is also configured to present representations of a supplemental, therapeutic bolus and of doses of a therapy schedule. In one example, the supplemental, therapeutic bolus may occur after a priming phase of IMD 12. A priming phase may generally refer to a delivery phase during which fluid is moved toward the distal tip of the catheter. Depending on the structure of the IMD, the priming phase may involve delivery of fluid from the reservoir, through internal tubing coupled to the reservoir, and to the tip of a catheter coupled to the tubing, such that the fluid is in a position to be infused into the patient when desired. The representations may indicate that a supplemental, therapeutic bolus that follows the priming phase is immediately followed by a regular, programmed dose specified by the therapy schedule of the dosing program, that the supplemental, therapeutic bolus overlaps the programmed dose of the therapy schedule, or that the programmed dose of the therapy schedule occurs soon after the supplemental, therapeutic bolus. In each case, there may be some risk of excessive dosage. User interface 82 allows a user, such as a clinician, to accept a pending dosing program that includes the therapy schedule and the therapeutic bolus, or to modify the dosing program to alter one or more programmed doses of the therapy schedule, the supplemental, therapeutic bolus, or other factors of the dosing program. The dosing program information may also be stored within memory 86 periodically during therapy, whenever external programmer 20 communicates within IMD 12, or only when the user desires to use or update the dosing program information.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12. The techniques described in this disclosure may be communicated between IMD 12 via any type of external device capable of communication with IMD 12.

External programmer 20 is one example of a programmer device that includes a user interface comprising a display to present a graphical representation of doses of fluid to be delivered to a patient via an implantable fluid delivery device, and a processor that controls the user interface. The processor may control the user interface to simultaneously present on the display a first graphical representation of a supplemental bolus to be delivered by the implantable fluid delivery device and a second graphical representation of programmed doses of a therapy schedule of the implantable fluid delivery device, such that at least a portion of the programmed doses of the therapy schedule follows delivery of the supplemental bolus by the implantable fluid delivery device.

Figure 4:
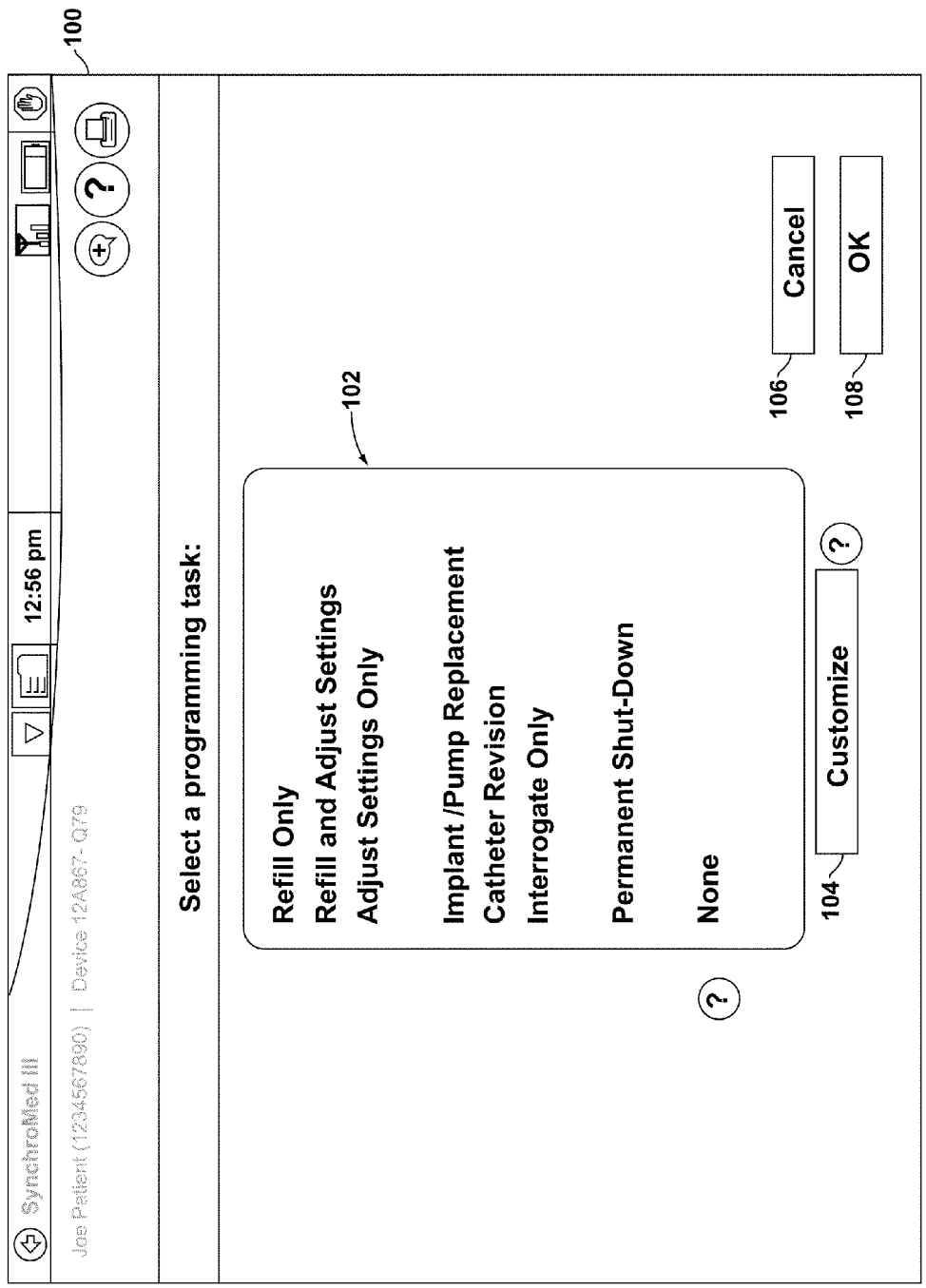
FIG. 4 is a screenshot illustrating an example user interface screen presented by an external programmer when a user first begins interacting with the programmer.

FIG. 4 is a screenshot illustrating an example user interface screen 100 presented by programmer 20 when a user first begins interacting with programmer 20. User interface screen 100 may be displayed by user interface 82 of programmer 20, and may present a task-oriented programming interface. When a user begins a session of working with programmer 20, programmer 20 presents user interface 100 to the user. The user may select from a variety of tasks 102 to perform using programmer 20. Tasks 102 of FIG. 4 depict example tasks "refill only," "refill and adjust settings," "adjust settings only," "implant/pump replacement," "catheter revision," "interrogate only," "permanent shut-down," and "none." Other examples may include additional or fewer tasks for the user to perform. In one example, processor 84 determines, from the selection of tasks 102, a series of task screens to present to the user of programmer 20 via user interface 82. Processor 84 may cause user interface 82 to present one or more task screens, each of which may receive one or more pieces of data from the user, in order to program IMD 12 according to the selected one of tasks 102. Programmer 20 may implement more task screens than are necessary for any one of tasks 102, therefore programmer 20 may not display unnecessary screens to the user. In this manner, programmer 20 may assist a user in efficiently programming IMD 12 by requesting relevant data without requesting unnecessary data. Programmer 20 may therefore minimize the number of screens that are displayed based on a selection from tasks 102.

The user may select one of tasks 102 from screen 100. For example, the user may select one of the tasks using a pointer controlled by a mouse. As another example, the user may select one of the tasks by touching the task on a touch-screen interface, e.g., with a finger or a stylus. The user may select Cancel button 106 to end the current session or, after selecting one of tasks 102, the user may select OK button 108 to perform the task. Upon receiving a selection of OK button 108, the user interface presents a different display screen to enable the user to perform the task with programmer 20. The user may also select Customize button 104 to customize the task selected from list 102, e.g., one or more parts or sub-parts of the task selected from list 102. In this manner, the user may select which of the one or more task screens are displayed.

Figure 5A:
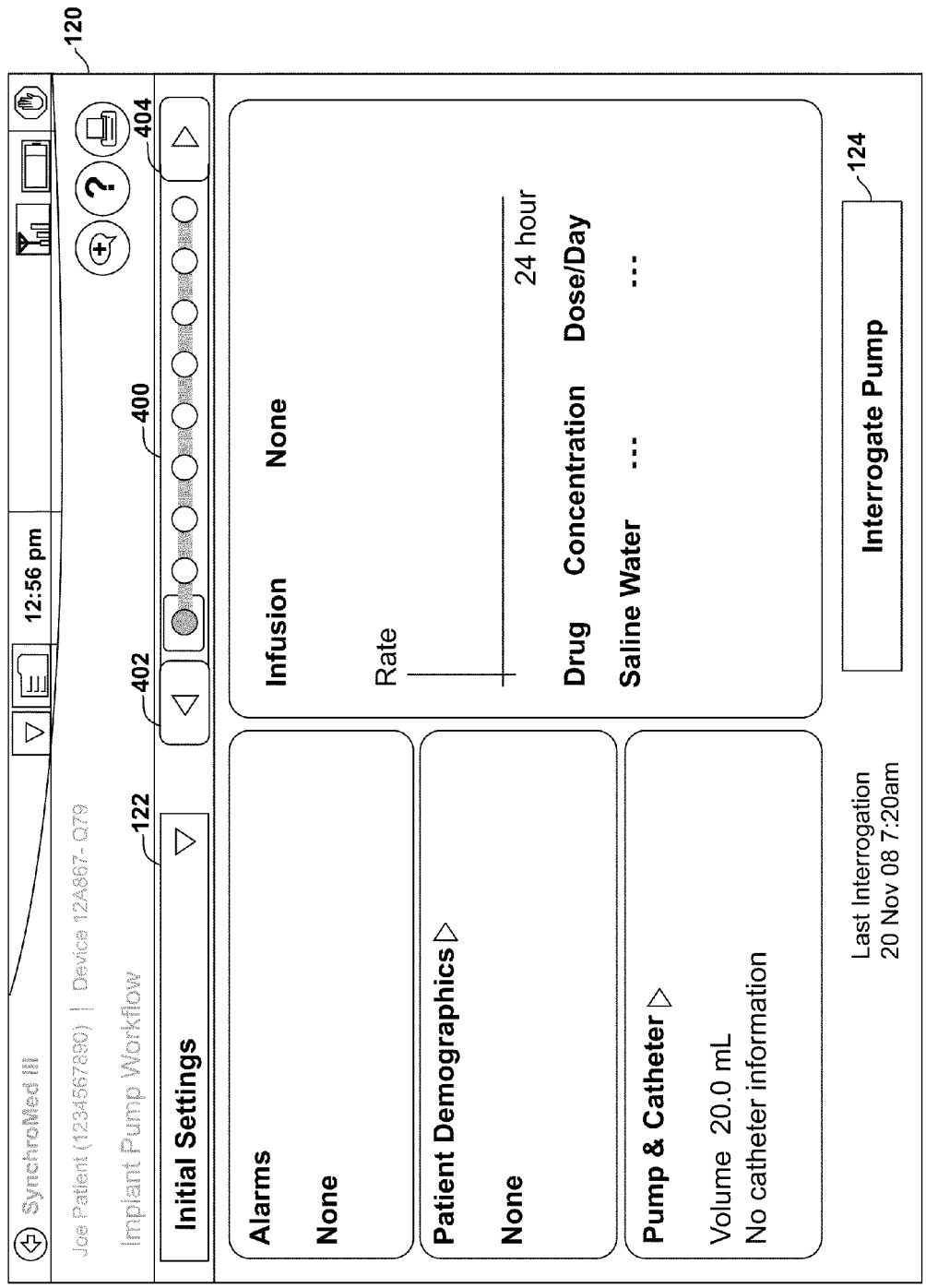
FIGS. 5A and 5B are screenshots illustrating an example user interface screen presented by an external programmer for configuring an implantable medical device.
Figure 5B:
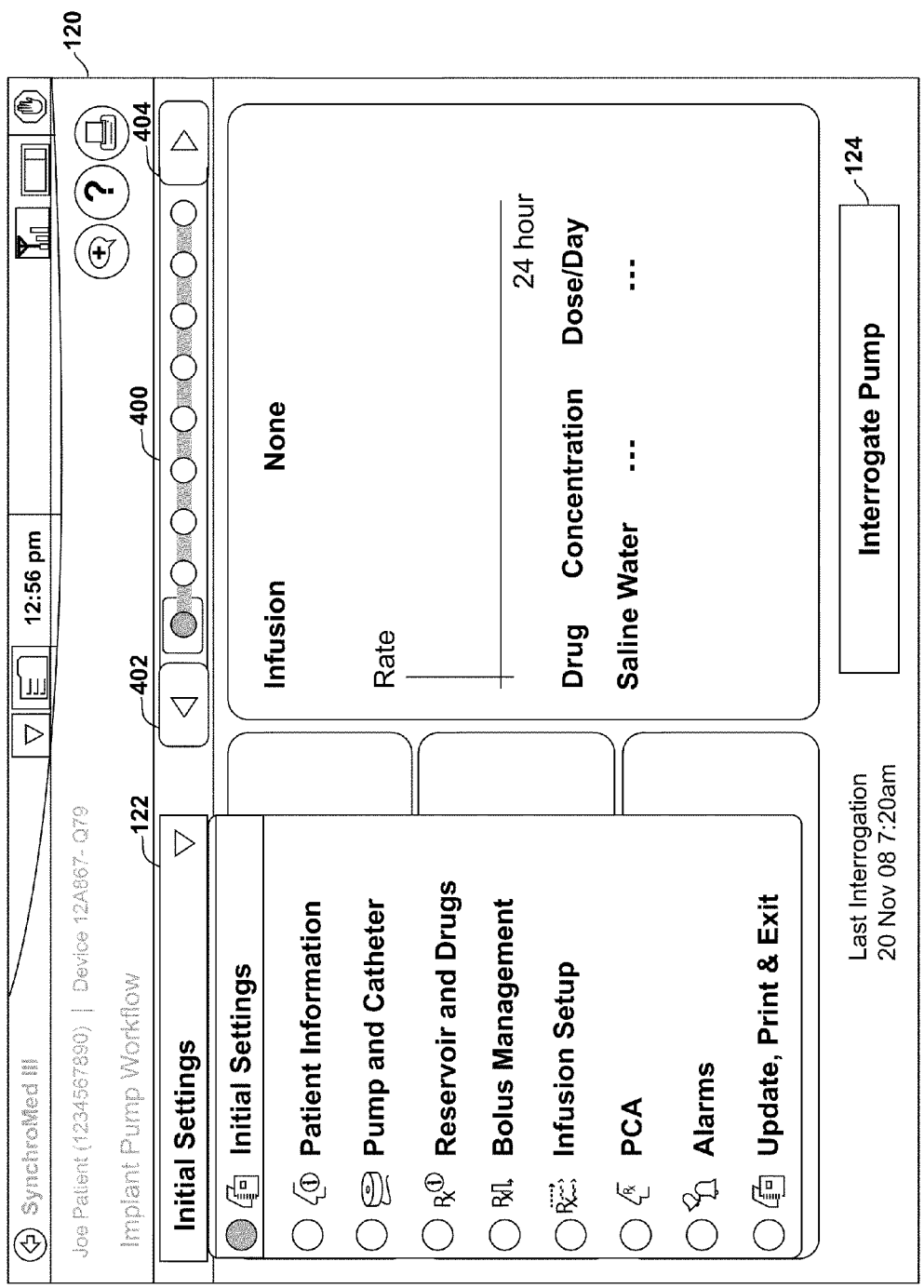

FIGS. 5A and 5B are screenshots illustrating an example user interface screen 120 for configuring IMD 12. User interface screen 120 may be displayed by user interface 82 of programmer 20. User interface screen 120 may be displayed, e.g., when a user selects the "implant/pump replacement" task from tasks 102 and then selects OK button 108 of user interface 100 (FIG. 4). FIG. 5A depicts current therapy program information for the current settings of an IMD, such as IMD 12, associated with the program. For example, the therapy program information may include alarms information, patient demographics information, pump and catheter information, drug information, and an infusion pattern in the example of FIG. 5A. In the example of FIG. 5A, there is no pertinent alarm information or patient demographics information. However, the pump and catheter information indicates that the pump has a volume of 20.0 milliliters (mL). The infusion pattern shows a rate of infusion over a 24 hour period, but is blank in the example of FIG. 5A. The user may select Interrogate Pump button 124 to populate programmer 20 with data stored on IMD 12. The user may elect to do this when IMD 12 has current patient data, but programmer 20 does not. For example, IMD 12 may have been programmed with a different programmer than programmer 20. The user may also select Interrogate Pump button 124 to retrieve data from IMD 12 that IMD 12 has collected during operation within patient 16.

The user may edit settings of the therapy program information by selecting various options from drop-down menu 122 (FIGS. 5A and 5B). FIG. 5B illustrates the options available in this example, which include "initial settings," "patient information," "pump and catheter," "reservoir and drugs," "bolus management," "infusion setup," "PCA," "alarms," and "update, print, and exit." When a user selects any of these options from drop-down menu 122, programmer 20 updates and refreshes user interface screen 120 to illustrate settings and options for the selected option, as discussed in greater detail below.

FIGS. 5A and 5B also include programming status indicator 400, left navigation arrow 402, and right navigation arrow 404. Programming status indicator 400 informs the user of where the user is in the programming process, e.g., in the process of developing a pending dosing program for IMD 12. Processor 84 may, according to instructions encoded within memory 86 of programmer 20, determine which screens are necessary to program IMD 12 based on input received with the example user interface screen of FIG. 4. The user may also navigate between screens using left navigation arrow 402 and right navigation arrow 404. In addition, the user may jump to a particular screen by selecting the screen from drop-down menu 122. When the user selects left navigation arrow 402, processor 84 may cause user interface screen 12082 to display a previous screen in the process of programming IMD 12. Similarly, when the user selects right navigation arrow 404, processor 84 may cause user interface screen 12082 to display a next screen in the process of programming IMD 12. Status indicator 400 may indicate whether the user has entered sufficient information in each screen, which screen the user is currently viewing, how many screens are remaining, or other information regarding the programming status of IMD 12.

Figure 6:
FIG. 6 is a screenshot illustrating an example user interface screen presented by an external programmer for editing patient information.

FIG. 6 is a screenshot illustrating an example user interface screen 120 for editing patient information 140, e.g., upon selection of "patient information" from drop-down menu 122 (FIG. 5B). User interface screen 120 displays patient information 140 when a user selects "patient information" from drop-down menu 122. The user may fill in fields of patient information 140 to save patient data to memory 86 of programmer 20, such that the patient information can be retrieved at a later time. This information may also assist the user in selecting a therapy regimen for patient 16. As shown in FIG. 6, the patient information 140 may include a variety of information, such as name, gender, address, identification number, and birth date, as well as various implant notes that may be recorded by a clinician with respect to the implant date, site, and physician for a particular patient.

Figure 7:
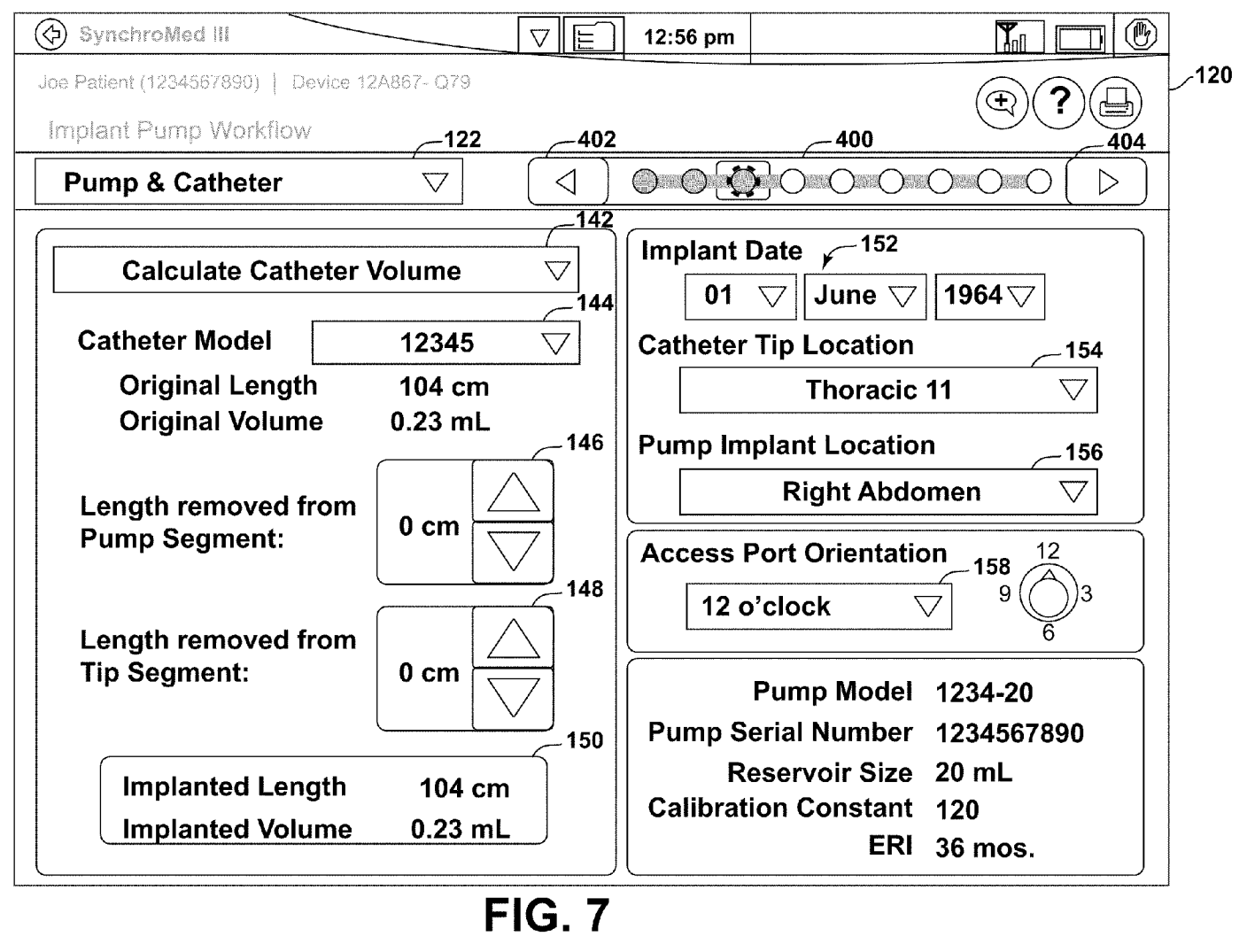

FIG. 7 is a screenshot illustrating an example user interface screen 120 for editing information relating to the fluid delivery pump and catheter implanted in a patient. User interface screen 120 displays information for editing fluid delivery pump and catheter information when the user selects "pump and catheter" from drop-down menu 122. For example, user interface screen 120 enables a user to describe catheter volume, a date of implantation of IMD 12, a location of IMD 12, and other information regarding IMD 12.

The user can select various methods for entering catheter volume from catheter volume drop-down menu 142. In the example of FIG. 7, the user has selected "calculate catheter volume," which causes programmer 20 to calculate the catheter volume from various data regarding the catheter. In another example, the user may select "enter catheter volume" from drop-down menu 142, e.g., when the user knows the volume of the catheter and desires to enter the volume directly, rather than having programmer 20 calculate the volume. In the example of FIG. 7, the user selects a catheter model from catheter model drop-down menu 144. Programmer 20 stores default values for potential catheter models for the catheter's length and volume before the catheter has been modified.

When fluid delivery pump IMDs are implanted in patients, surgeons commonly remove one or more segments from the catheter of the IMD in order to properly size the catheter for implantation. To determine a proper bolus amount for priming, the surgeon who removed this segment from the IMD must record the length of the segment removed. The user of programmer 20 may therefore enter the length of the segment removed from the catheter using user interface screen 120 by selecting the length removed from the pump segment with arrows 146 and the length removed from the tip segment with arrows 148. When user interface screen 120 receives removed-length data from arrows 146 and 148, user interface screen 120 sends the data to processor 84, which calculates a resulting length for the catheter, as well as a resulting volume for the catheter, e.g., in accordance with a program or module stored in memory 86. The processor 84 then returns the results to be displayed on user interface screen 120, and user interface screen 120 displays the resulting implanted length and the resulting implanted volume for the catheter in output box 150.

User interface screen 120 also allows a user to enter a date that IMD 12 was implanted with boxes 152. The user also may enter a location where the tip of catheter 18 of IMD 12 was implanted using drop-down menu 154, as well as a location of IMD 12 itself using drop-down menu 156. In the example of FIG. 7, the catheter tip location is indicated as "Thoracic 11," and the pump implant location is indicated as "right abdomen." A subsequent user of programmer 20 may therefore determine the location of IMD 12, e.g., to refill reservoir 30 of IMD 12 with fluid. The user also enters the orientation of the access port, e.g., 12 o'clock in the example of FIG. 7, using drop-down menu 158. The orientation of the access port assists a user in determining the location and orientation of refill port 26 of IMD 12. Various pump information such as pump model, serial number, reservoir size, calibration constant and elective replacement indicator (ERI) may be presented on the screen of FIG. 7.

Figure 8:
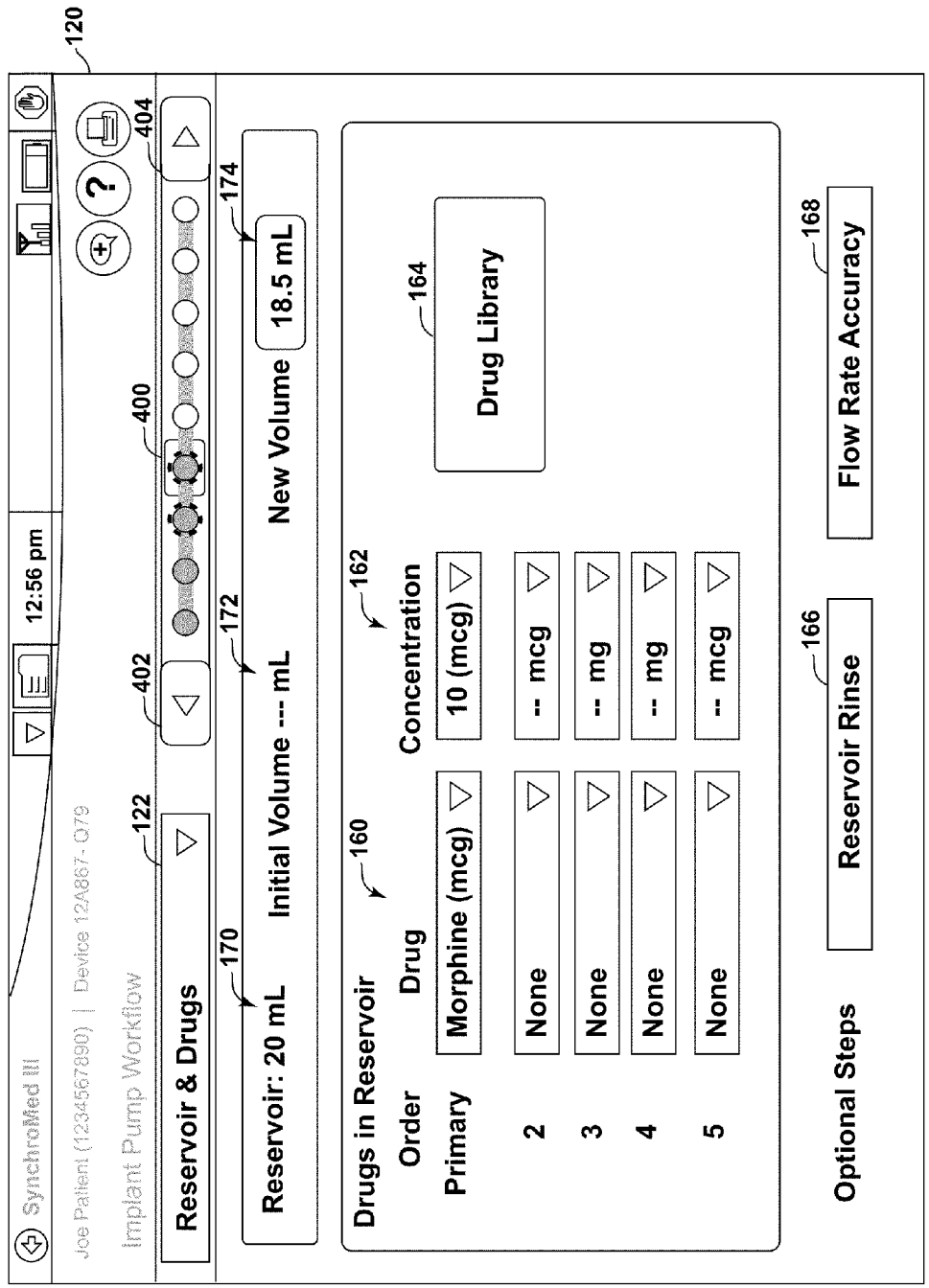
FIG. 8 is a screenshot illustrating an example user interface screen presented by an external programmer for editing drug information regarding a drug delivered by an implantable medical device.

FIG. 8 is a screenshot illustrating an example user interface screen 120 for editing therapy program information including drug information regarding a drug delivered by IMD 12. User interface screen 120 enables a user to modify drug information for drugs delivered by IMD 12. Therefore, when a subsequent user interrogates IMD 12, the subsequent user may determine the information regarding the drug delivered by IMD 12.

User interface screen 120 depicts reservoir information that indicates a maximum volume 170 of reservoir 30 of IMD 12, a starting or initial volume 172 of drug within reservoir 30 as of the time of the programming session, and a new volume 174 that will be inserted into reservoir 30 after the programming session has been completed. In one example, IMD 12, programmer 20, or both, determine initial volume 172 at the beginning of a programming session by subtracting the dispensed volume of drug delivered to patient 16 since the last programming session from the new volume 174 entered at the time of the last programming session. The dispensed volume can be determined by multiplying the rate of drug delivery (volume/time) by the amount of elapsed time drug was dispensed at that rate.

The user may also enter drug information into drug selection area 160 and concentration selection area 162. The user may select a drug from a drop-down menu of drug selection area 160 that is to be delivered to reservoir 30 of IMD 12. The user may also select a corresponding concentration of the drug from a corresponding drop-down menu of concentration selection area 162. Example drugs that may be listed by drop-down menus of drug selection area 160 include saline (as a default filler or as a placebo during clinical testing or other drug trails), morphine, bupivacaine, clonidine, hydromorphone, baclofen, alpha adrenergic agonists, baclofen, fentanyl, sufentanil, ziconotide, or other drugs or fluids. Selecting drugs from multiple drop-down menus of drug selection area 160 indicates that a combination of drugs is to be delivered to reservoir 30. For example, a user may select "morphine" from a first drop-down menu and "bupivacaine" from a second drop-down menu of drug selection area 160. When IMD 12 has already been programmed according to a dosing program with a first fluid, i.e., a fluid containing a drug at a particular concentration, user interface screen 120 displays the first drug and the first concentration of the drug. If the user changes the drug, processor 84 may recognize the fact that the drug and/or concentration has changed and may cause user interface screen 120 to suggest that a bridge be performed.

The user may also select Drug Library 164 to link to a drug library. User interface screen 120 may then display a list of drugs and information regarding each of the listed drugs, such as names of the drugs, one or more common concentration values, and units for the values. In one example, the user may select a drug from the drug library, including a concentration of the drug, and user interface screen 120 populates one or more of drop-down menus 160 and/or 162 with the user's selection. In one example, the user may select a drug from the drug library, including a concentration of the drug, and user interface screen 120 populates one or more of drop-down menus 160 and/or 162 with the user's selection. In one example, the drug library may be user definable, allowing a user to enter names of drugs, one or more concentrations that are used for the drugs, and units for the concentrations. The user may also perform optional steps during the programming session, such as performing a reservoir rinse to rinse reservoir 30 of IMD 12 by selecting reservoir rinse button 166 or determining flow rate accuracy of IMD 12 by selecting flow rate accuracy button 168.

Figure 9:
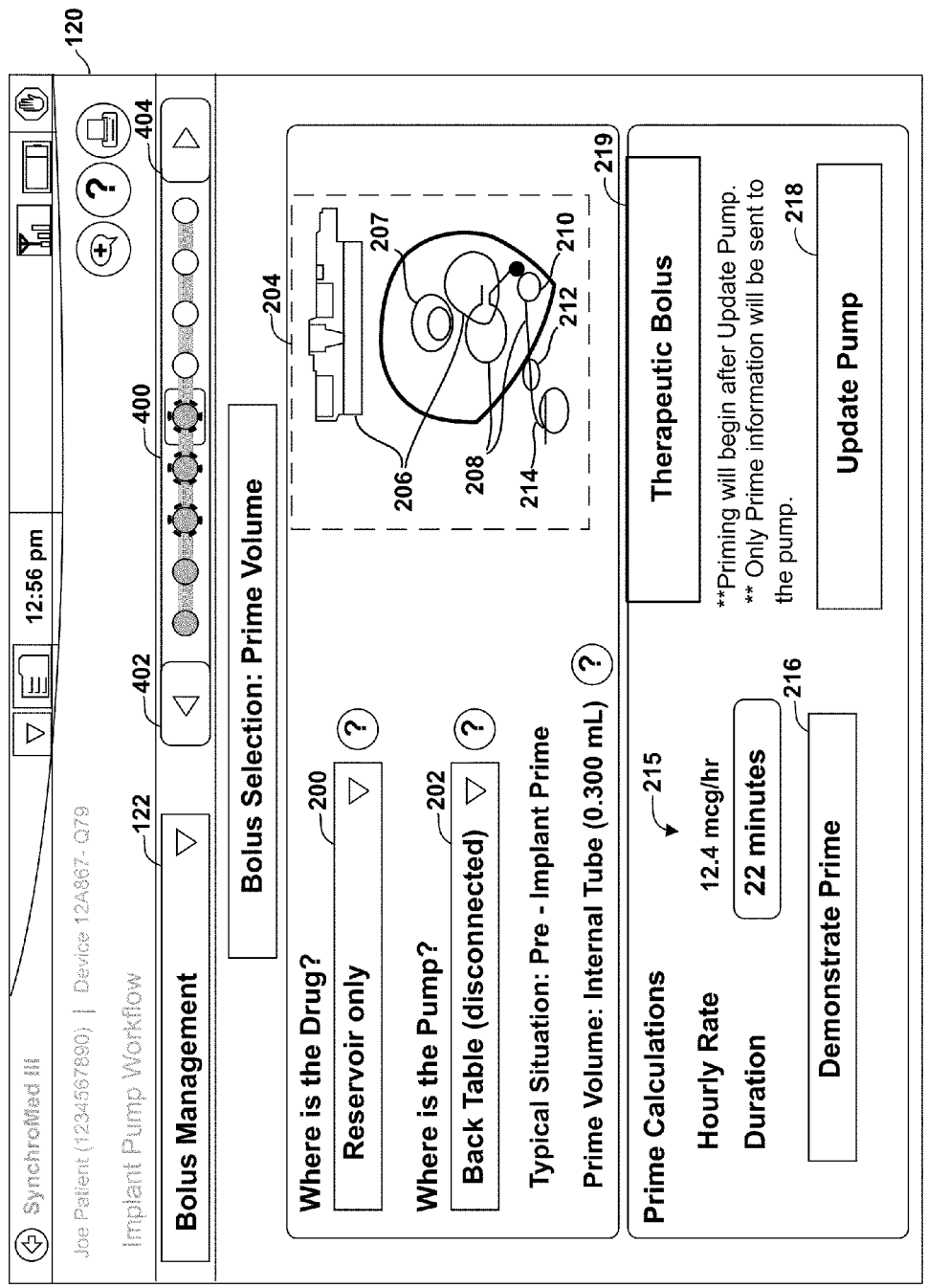
FIG. 9 is a screenshot illustrating an example user interface screen presented by an external programmer for setting up a priming phase of an implantable medical device.

FIG. 9 is a screenshot illustrating an example user interface for setting up a priming phase of IMD 12. User interface screen 120 presents pictorial representation 204 of IMD 12. Pictorial representation 204 need not include representations of all of the features of IMD 12, and may include a portion of IMD 12, e.g., one or more portions of IMD 12 at which a fluid may be present. For example, pictorial representation 204 includes reservoir illustration 206, which is a pictorial representation of reservoir 30 of IMD 12, refill port illustration 207, which is a pictorial representation of refill port 26 of IMD 12, internal tubing illustration 208, which is a pictorial representation of internal tubing 32 of IMD 12, pump illustration 210, which is a pictorial representation of fluid delivery pump 46, catheter access port illustration 212, which is a pictorial representation of catheter access port 36 of IMD 12, and catheter illustration 214, which is a pictorial representation of catheter 18 of IMD 12.

User interface screen 120 presents prime calculations 215 that satisfy priming requirements of IMD 12. That is, prime calculations 215 define a rate at which to deliver fluid, and a time during which IMD 12 should deliver the fluid at the rate, to ensure that the fluid reaches the tip of catheter 18. In the example depicted in FIG. 9, prime calculations 215 include an hourly rate of 2 mL/hr and a duration of 22 minutes. These calculations may be based on the location of the drug, the length of the internal tubing of IMD 12, and the length of catheter 18. The user may modify the setup of the priming phase by changing the rate to deliver the fluid or the time during which to deliver the fluid at the rate via user interface screen 120. The user may also select Demonstrate Prime button 216, Update Pump button 218, or Therapeutic Bolus button 219. When the user selects Demonstrate Prime button 216, user interface screen 120 may depict a demonstration of a priming phase of IMD 12, e.g., a location of the fluid and movement of the fluid through IMD 12. Again, a priming phase refers to delivery of a priming bolus to fill the catheter with fluid up to the distal tip of the catheter, so that the IMD is ready to deliver fluid from the distal tip to the patient to support a regular dosing program. During the priming phase, the patient generally does not receive fluid. Upon completion of the priming phase, a supplemental bolus may be delivered to quickly restore therapeutic effects. When the user selects "Update Pump" button 218, programmer 20 transmits the dosing program to IMD 12 via telemetry module 88. When the user selects Therapeutic Bolus button 219, user interface screen 120 presents a window that allows the user to program a supplemental, therapeutic bolus, e.g., with the example of FIG. 10.

Figure 10:
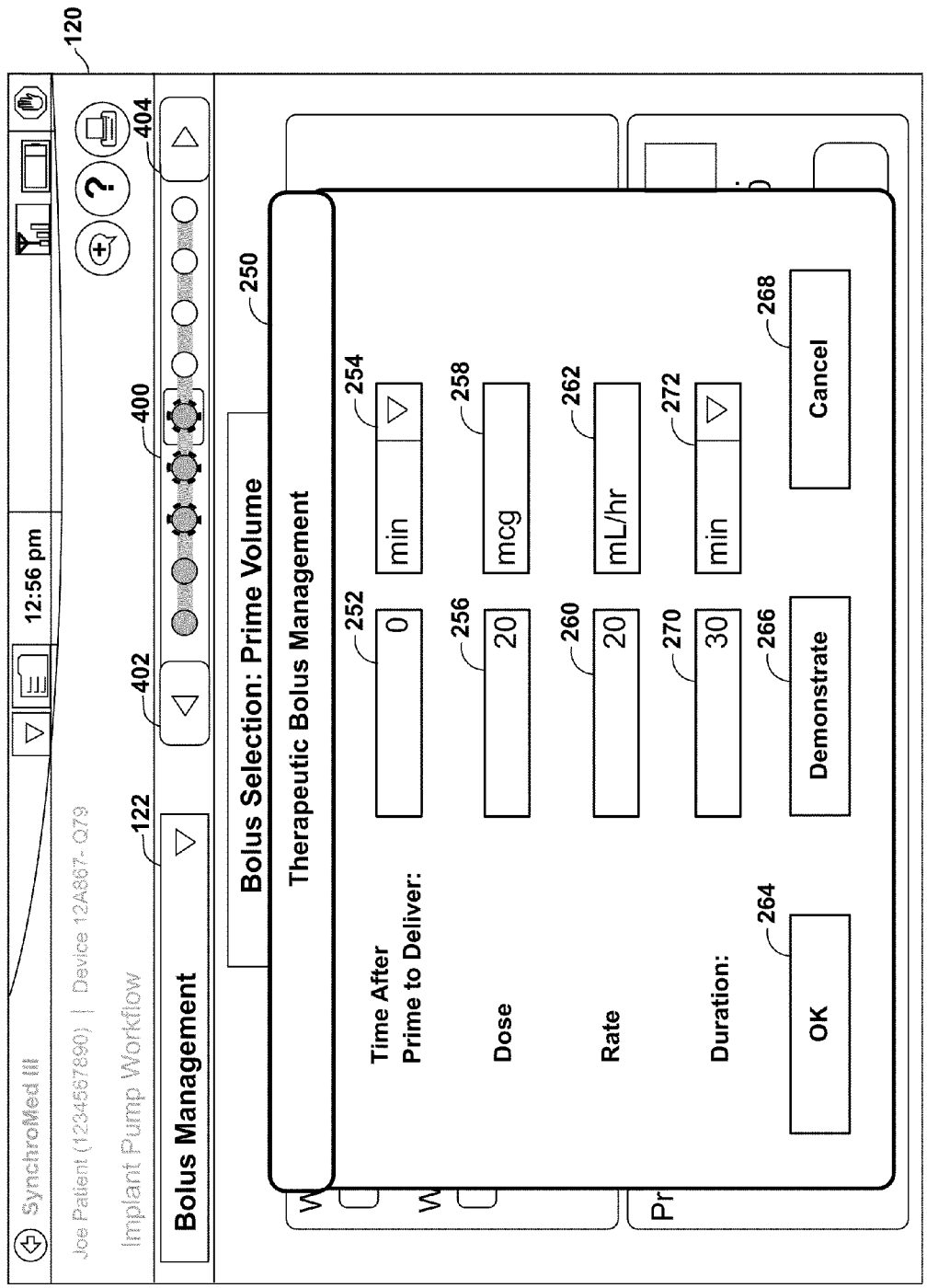
FIG. 10 is a screenshot illustrating an example user interface screen presented by an external programmer for programming a therapeutic bolus to be delivered by an implantable medical device.

FIG. 10 is a screenshot illustrating an example user interface for programming a therapeutic bolus delivered by IMD 12. IMD 12 may deliver a therapeutic bolus in addition to doses of a therapy schedule delivered in accordance with a dosing program. For example, when an old IMD is replaced with new IMD 12, patient 16 may not have received a treatment that was being delivered by the old IMD for a lengthy period of time. Therefore, a user of programmer 20 may program IMD 12 to deliver a therapeutic bolus immediately or soon after completion of a priming phase of IMD 12, i.e., after a period of time when IMD 12 runs fluid delivery pump 46 to move fluid to the tip of catheter 18. Window 250 of FIG. 10 enables the user to program such a therapeutic bolus after a priming phase of IMD 12. When the priming phase runs its course, IMD 12 may deliver the therapeutic bolus immediately or following a specified delay period. A window similar to window 250 may be presented by user interface 82 of programmer 20 to enable a user to program an extra therapeutic bolus in addition to the therapeutic bolus following the priming phase of IMD 12, e.g., times not corresponding to a priming phase of IMD 12. For example, the user may program a supplemental, therapeutic bolus after selecting "therapeutic bolus" from window 286 of FIG. 13, as discussed with respect to FIG. 13 below.

Window 250 is presented after the user selects Therapeutic Bolus button 219 (FIG. 9). Window 250 includes text fields 252, 256, 270 and drop-down menus 254, 258, 272. The user may enter a time interval as a specified delay period after completion of the priming phase of IMD 12 at which to deliver the therapeutic bolus in text field 252 as a numeric representation, such as an integer, and select units for the interval for drop-down menu 254. Drop-down menu 254 may include time options such as, for example, seconds, minutes, or hours. The user may enter dosage information in text field 256 corresponding to a quantity of drug or volume of fluid to be delivered to patient 16 as an integer. Text field 258 represents units of a dose of drug/volume of fluid, for example, micrograms (mcg) or milliliters (mL), as selected at, e.g., the user interface of FIG. 8, or as calculated by processor 84. The user may, alternatively, enter a desired rate of delivery in text field 260, and user interface screen 120 may display units for the rate of delivery in text field 262.

The user may also enter a time duration as an integer for the therapeutic bolus in text field 270 corresponding to a time over which the therapeutic bolus is to be delivered, such that the full dose entered in text field 256 is delivered at the end of the duration of the therapeutic bolus. The user may also select the units for the duration from drop-down menu 272, which may include options such as seconds, minutes, and hours. In the example of FIG. 10, the user may either enter a desired dose of drug, or a desired rate of delivery, and processor 84 may calculate the other measurement based on the time duration entered in text field 270. That is, if the user enters a desired dose in text field 256, processor 84 may calculate the rate of delivery based on the entry in text field 270. Alternatively, if the user enters a desired rate of delivery, processor 84 may calculate the dosage to be delivered based on the entry in text field 270. Using the information entered via window 250, programmer 20 programs IMD 12 to deliver the amount of fluid over the specified duration of time to support the delivery of the therapeutic bolus.

Window 250 also includes OK button 264, Demonstrate button 266, and Cancel button 268. The user may select OK button 264 to indicate that the settings entered in text fields 252, 256, 270 and drop-down menus 254, 258, 272 should be used for the therapeutic bolus following the priming phase of IMD 12. The user may select Demonstrate button 266 to request a demonstration of a fluid delivery schedule resulting from scheduling a supplemental bolus and a therapy schedule of a dosing program, e.g., as discussed with respect to FIGS. 11A-11C. The user may select Cancel button 268 to cancel programming of a therapeutic bolus.

Figure 11A:
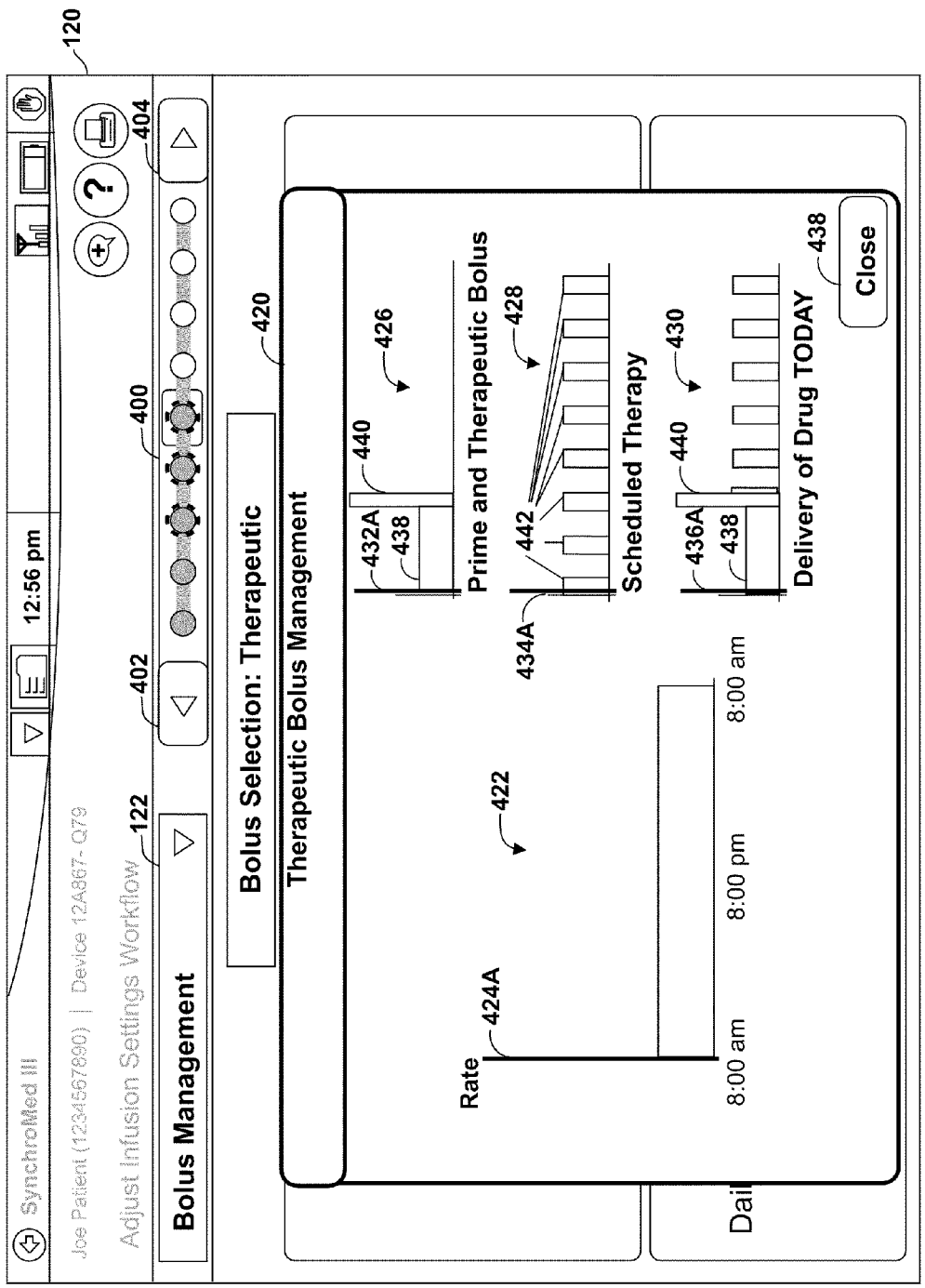
FIGS. 11A-11C are screenshots illustrating an example user interface screen that depicts a representation of a supplemental bolus and a representation of a therapy schedule of a dosing program.
Figure 11B:
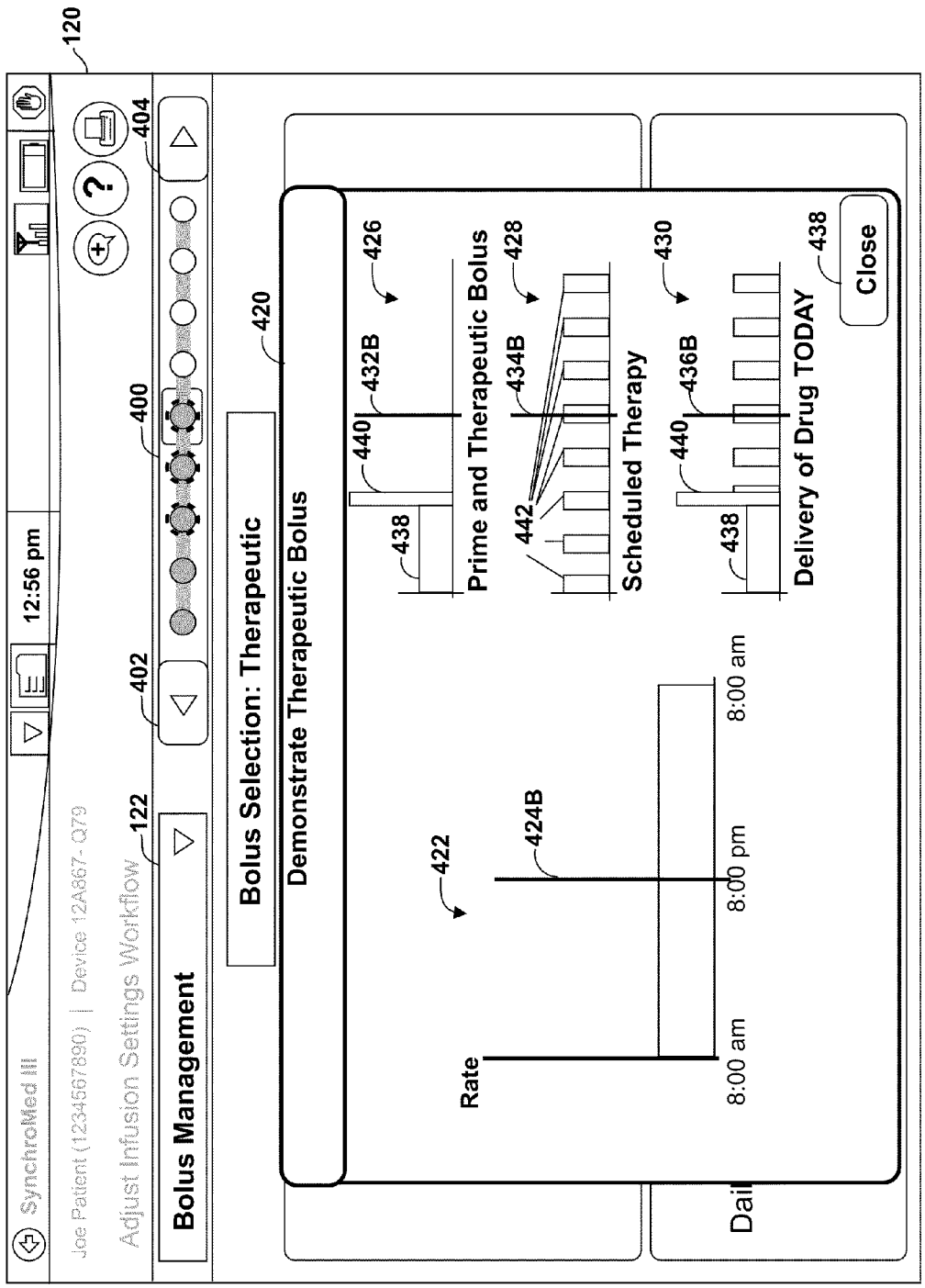
Figure 11C:
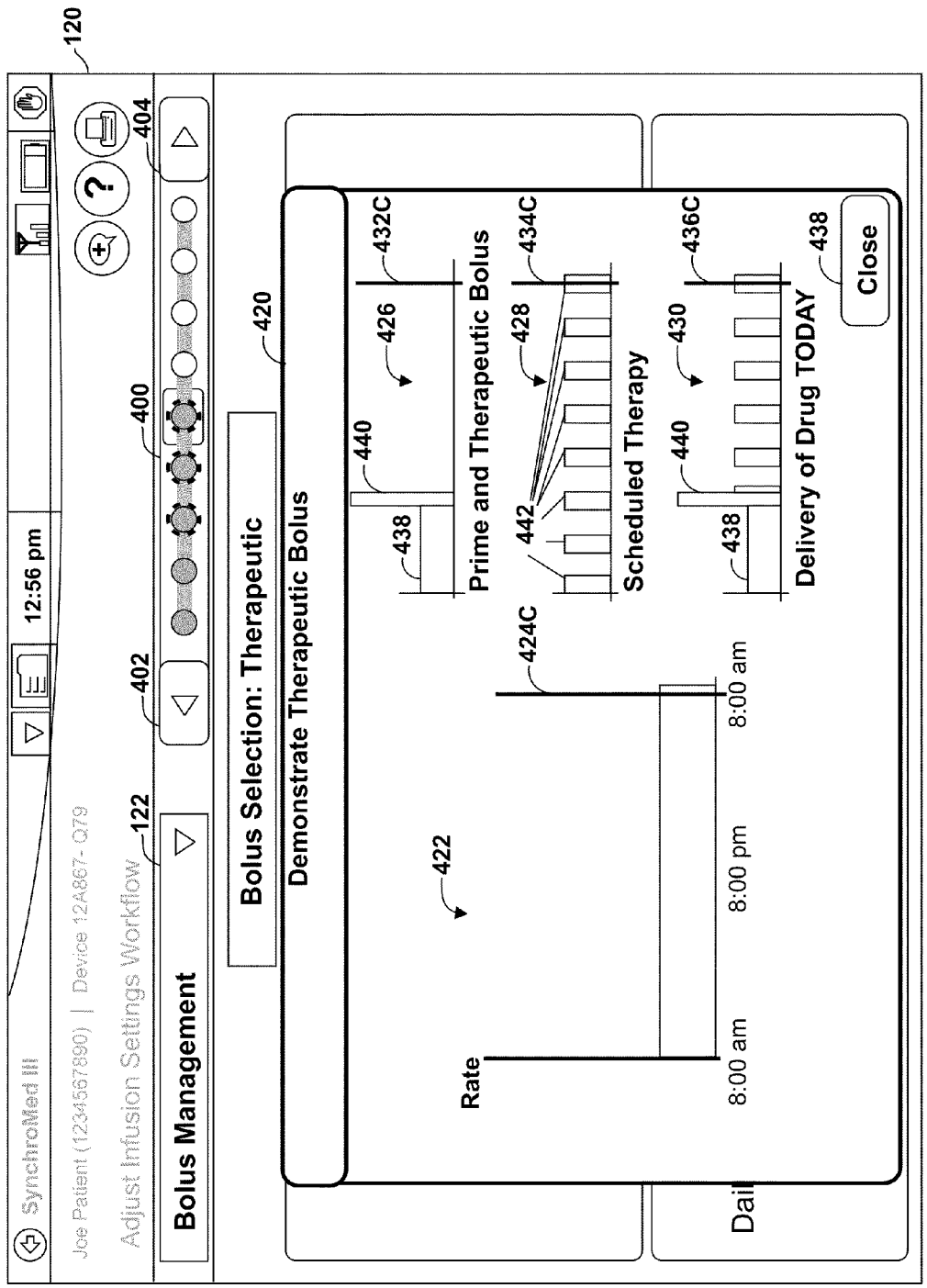

FIGS. 11A-11C are screenshots illustrating an example user interface that depicts a representation of a supplemental bolus and a representation of a therapy schedule of a dosing program. The supplemental bolus in FIG. 11A is identified as a therapeutic bolus. In the example, window 420 includes graph 422 that represents a 24-hour time period during which IMD 12 delivers the supplemental bolus and programmed doses of the therapy schedule. User interface screen 120 causes status indicator 424 to move along graph 422 as a representation of a progression of time. User interface screen 120 also presents priming phase and therapeutic bolus graph 426, therapy schedule graph 428, and combined graph 430. Priming phase and therapeutic bolus graph 426 includes priming phase representation 438 and therapeutic bolus representation 440. Therapy schedule graph 428 includes programmed dose representations 442. User interface 430 depicts the resulting fluid delivery schedule in graph 430. That is, combined graph 430 represents the actual fluid delivery schedule of IMD 12. In the example, the fluid delivery schedule represented by combined graph 430 includes priming phase representation 438, supplemental, therapeutic bolus representation 440, and programmed dose representations 442 following supplemental, therapeutic bolus representation 440. In this manner, a user may readily observe when the priming phase will occur, when the therapeutic bolus will be delivered, and when each of the programmed doses will be delivered.

FIG. 11A presents a display corresponding to a beginning of a 24-hour period. Therefore, status indicator 424A is represented at the beginning of graph 422. User interface screen 120 also presents status indicators 432, 434, 436 for each of graphs 426, 428, 430, respectively. Status indicators 432, 434, 436 correspond to status indicator 424. Accordingly, in the example of FIG. 11A, status indicators 432A, 434A, 436A are depicted at the beginning of each of graphs 426, 428, 430, respectively. As user interface screen 120 causes status indicator 424 to move to the right along graph 422, user interface screen 120 simultaneously causes status indicators 432, 434, 436 to move to the right along graphs 426, 428, 430. In one example, a user may select any one of status indicators 424, 432, 434, 436 to "click and drag" the status indicator either left or right, and user interface screen 120 automatically causes the other status indicators to move accordingly. In the example of FIGS. 11A-11C, a supplemental, therapeutic bolus indicated by supplemental bolus representation 440 is programmed to occur in an overlapping manner with a regular dose indicated by dose representations 442. Upon viewing user interface screen 120, the clinician may visually identify the overlap and identify a situation in which an undesirably large dose could be applied due to the combination of the therapeutic bolus and regular dose. In this case, the clinician may be prompted to take action to modify either the supplemental bolus, the dosing program, or the relative timing between them to avoid an undesirably large dose.

FIG. 11B presents a display corresponding to approximately a midpoint of the 24-hour period. Accordingly, user interface screen 120 presents status indicator 424B approximately half-way through graph 424, and status indicators 432B, 434B, 436B approximately half-way across graphs 426, 428, 430. Similarly, FIG. 11C presents a display corresponding to approximately the end of the 24-hour period, therefore user interface screen 120 presents status indicator 424C approximately at the end of graph 424, and status indicators 432C, 434C, 436C approximately at the end of graphs 426, 428, 430.

FIGS. 11A-11C are examples of screenshots for displaying, with a device for programming an implantable fluid delivery device, a first graphical representation of a supplemental bolus to be delivered by the implantable fluid delivery device and displaying, simultaneously with the first graphical representation, a second graphical representation of programmed doses of a therapy schedule to be delivered by the implantable fluid delivery device.

Figure 12:
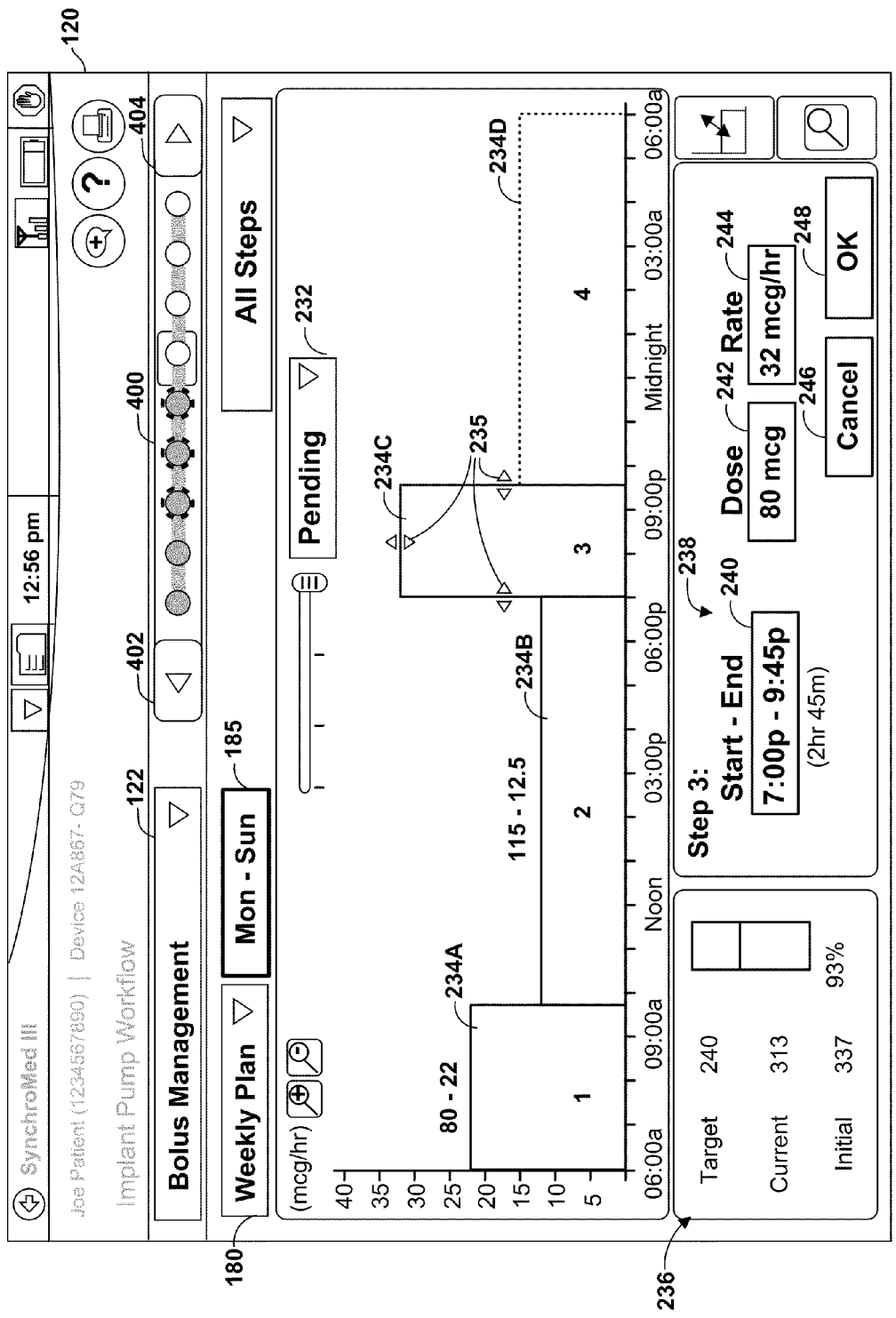
FIG. 12 is a screenshot illustrating an example user interface screen presented by an external programmer by which a user may modify an infusion pattern to be administered by an implantable medical device.

FIG. 12 is a screenshot illustrating an example user interface by which a user may modify an infusion pattern. The example infusion pattern of FIG. 12 is an "All Steps" infusion pattern, as indicated by drop-down menu 187. An all-steps infusion pattern includes a plurality of steps, such as steps 234A-234D (steps 234), each of which has a time and a dose. The time of the step corresponds to the width of the step, and the dose rate of the step corresponds to the height of the step. Different doses may have different dose rates, including zero dose rate in some instances.

In the example of FIG. 12, step 234A has a height corresponding to 22 mcg/hour and a width corresponding to 3 hours and 38 minutes. Step 234B has a height corresponding to 12.5 mcg/hour and a width corresponding to 9 hours and 12 minutes. Step 234C has a height corresponding to 32 mcg/hour and a width corresponding to 2 hours and 45 minutes. Step 234D is illustrated with a dashed line outline to indicate that step 234D has not yet been configured.

As illustrated in the example of FIG. 12, the user is in the process of editing step 234C by dragging one or more of arrows 235 either up, down, left, or right. By dragging arrows 235, the user may change the infusion pattern of step 234C. For example, the user may drag one of arrows 235 to the right to increase the time during which the dose rate is to be delivered. The user may also drag one of arrows 235 up to increase the dose rate for step 234C. In one example, programmer 20 receives and stores a start time for each of steps 234 and a duration from the start time for each of steps 234, e.g., in memory 86. Programmer 20 may therefore retrieve the start time and duration for each of steps 234 from memory 86 to display representations of doses of the therapy program comprising steps 234 at proper locations of the user interface, e.g., as discussed with respect to the example of FIG. 14. In another example, programmer 20 may receive a start time and an end time for each of steps 234 and store the start and end times in memory 86.

User interface screen 120 also provides summary information regarding the pending infusion pattern. For example, user interface screen 120 displays window 236, which illustrates the total dose of a drug that will be delivered according to programmed steps 234, e.g., according to initial programming of IMD 12, pending programming of IMD 12, and a target for the programming, as well as a representation of a percentage of the target dose that has been fulfilled, in the example of FIG. 12. Window 236 indicates that, in the example, the programmed 24-hour dose will deliver 313 mcg of drug to patient 16. Window 236 also illustrates that the target dose for the 24-hour period is 240 mcg, as well as the percent of the target met by the currently programmed 24-hour doses. Window 236 further displays an initial 24-hour dose, representing the 24-hour dose of a previous infusion pattern, which is 337 mcg in the example of FIG. 12.

User interface screen 120 also may display step-specific information 238. In the example of FIG. 12, step-specific information 238 corresponds to step 234C (step 3). Step-specific information includes start-and-end time text field 240, which corresponds to the width of step 234C. Dose text field 242 corresponds to a calculation of the total quantity of drug to be delivered to patient 16 during step 234C by IMD 12. Rate text field 244 depicts the rate at which a drug is to be delivered to the patient during step 234C, corresponding to the height of step 234C. In one example, the user may enter data in text fields 240-244 and the corresponding step, e.g., step 234C, will change shape automatically, without the user needing to move the step with arrows 235. In one example, user interface screen 120 may display soft keys, arrows, buttons, drop-down menus, or other means for modifying text fields 240-244. The user may also modify text fields 240-244 using a keyboard or other peripheral device attached to programmer 20, in other examples. The user may select OK button 248 to accept a current infusion pattern or Cancel button 246 to cancel programming of the infusion pattern and return to a previous screen.

Figure 13:
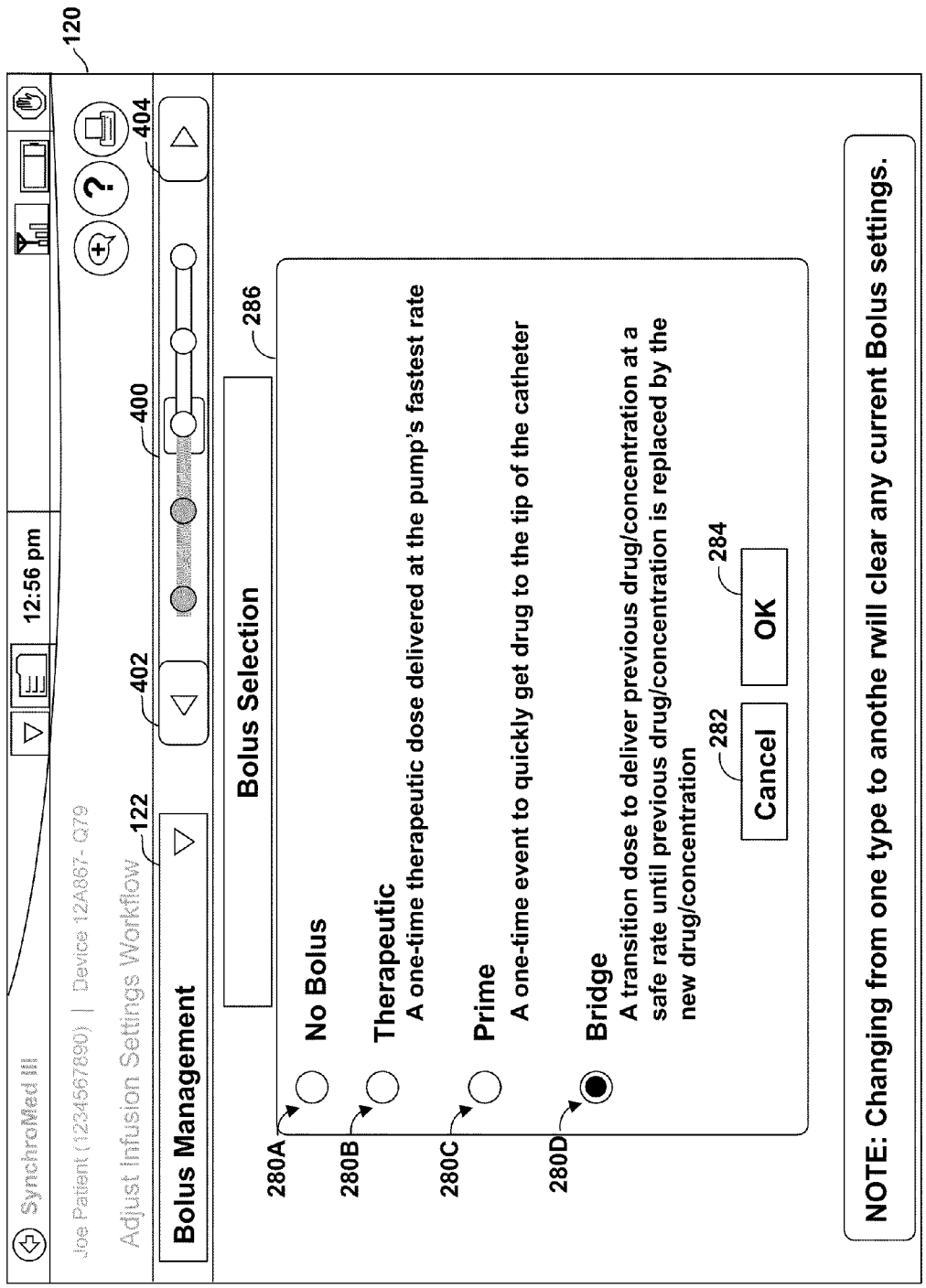
FIG. 13 is a screenshot illustrating an example user interface screen presented by an external programmer for selecting a type of bolus to program.

FIG. 13 is a screenshot illustrating an example user interface for selecting a type of bolus to program. A bolus may be programmed instead of or in addition to delivery of a regular dosing program. In some cases, for example, a regular dosing program may be preceded by a supplemental, therapeutic bolus, a prime bolus, and/or a bridging bolus. User interface screen 120 may present window 286 which enables a user to select a type of bolus to program for IMD 12. Window 286 includes radio buttons 280A-280D (radio buttons 280), Cancel button 282, and OK button 284. The user may select radio button 270A to stop IMD 12 from delivering any boluses, radio button 280B to program a therapeutic bolus, radio button 280C to program a priming bolus, or radio button 280D to program a bridging bolus. The user may then select OK button 284 to program the selected bolus in accordance with the selection of one of radio buttons 286. The user may also select Cancel button 282 to not program a bolus and to return to a previous screen.

Figure 14:
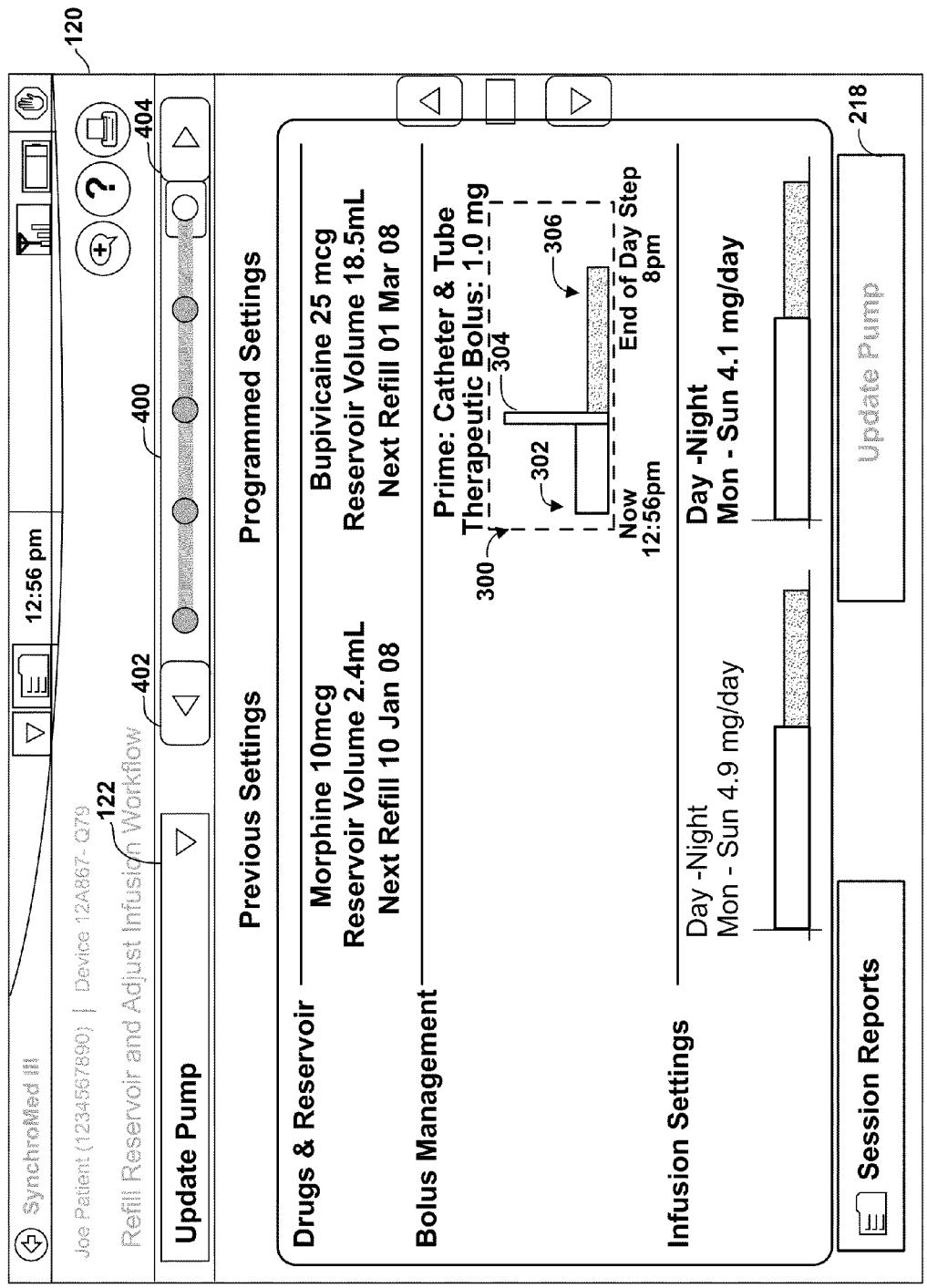
FIG. 14 is a screenshot illustrating an example user interface screen presented by an external programmer for displaying a representation of a therapeutic bolus simultaneously with a representation of a bolus as part of a therapy schedule.

FIG. 14 is a screenshot illustrating an example user interface that displays a representation of a supplemental, therapeutic bolus simultaneously with a representation of a dose of a therapy schedule. Graph 300 includes therapeutic bolus representation 304 and therapy schedule dose representation 306. In addition, graph 300 includes priming bolus representation 302. To display graph 300, user interface screen 120 retrieves a start time and a duration for each of therapeutic bolus representation 304, priming bolus representation 302, and therapy schedule dose representation 306. In one example, user interface screen 120 may retrieve a start time and an end time for each of therapeutic bolus representation 304, priming bolus representation 302, and therapy schedule dose representation 306. In the example of FIG. 14, user interface screen 120 displays therapeutic bolus representation 304 with gray shading, priming bolus representation 302 with white shading, and therapy schedule dose representation 306 with black shading. In other examples, user interface screen 120 may distinguish between the representations of a priming bolus, a therapeutic bolus, and doses of a therapy schedule using different shading, fill colors, outlining line styles, hatching marks, outline coloring, or other distinguishing characteristics.

For certain cases, user interface screen 120 may determine that an overlap of the therapeutic bolus and a dose of the therapy schedule has occurred or will occur, e.g., by determining that the start time of the dose of the therapy schedule occurs between the start time of the therapeutic bolus and the end time of the therapeutic bolus. That is, processor 84 of programmer 20 may compare the start time of the dose of the therapy schedule to the start time of the therapeutic bolus and/or to the end time of the therapeutic bolus. Processor 84 may compare these times to determine temporal proximity, overlap, or other temporal relationships between doses of the therapy schedule, the therapeutic bolus, a priming phase, a bridging phase, or other fluid delivery phases of IMD 12. In cases where overlap is determined to occur, user interface screen 120 may display a representation of the overlap, e.g., with a dashed line, different shading, different hatch marks, a different color, an arrow with a textual representation, a highlighted, blinking or flashing region, or by other means.

Under certain circumstances, patient 16 may not receive a dose as part of a therapy schedule for an extended period of time, e.g., minutes or hours, such as when IMD 12 replaces an old IMD, when IMD 12 is flushed, or under other circumstances. A gap in the delivery of a dose from IMD 12 to patient 16 under these circumstances may cause patient 16 discomfort. By delivering a supplemental bolus, such as a therapeutic bolus, IMD 12 may address the discomfort and possibly prevent the need for providing patient 16 with a different drug administered orally or intrathecally, which may require administering doctors to check whether two drugs conflict when used in conjunction. That is, patient 16 may continue to receive the original drug, rather than a combination of different drugs. A user of programmer 20 may therefore program a supplemental, therapeutic bolus using the user interface of FIG. 10, e.g., after a priming phase of IMD 12, to quickly restore therapeutic effect.

The supplemental, therapeutic bolus may permit patient 12 to immediately receive a dose to thereby restore therapeutic effects, such as pain relief or relief of other symptoms, instead of waiting for a regular dose according to the therapy schedule of the applicable dosing program. In accordance with the therapy schedule of the dosing program, IMD 12 may not deliver a dose of fluid for some time after completion of a priming phase, depending on the programmed timing of the therapy schedule. In other cases, however, the therapy schedule may specify a dose of fluid to be delivered in close proximity to a therapeutic bolus. The user may not realize that the supplemental, therapeutic bolus will be delivered in close proximity to a regular dose according to a therapy schedule of a dosing program. For example, a supplemental bolus may be delivered immediately before, overlapping with, or in close proximity to the dose of the therapy schedule, depending on the timing of the therapy schedule and, in some cases, the time the priming is completed.

User interface screen 120 therefore presents graph 300, which presents supplemental, therapeutic bolus representation 304 and therapy schedule dose representation 306 as graphical representations. The user may therefore readily observe a temporal relationship of therapeutic bolus representation 304 and therapy schedule dose representation 306, and levels of such boluses and doses, and determine whether the therapeutic bolus and the dose of the therapy schedule may administer too much drug to patient 16 too quickly. In this manner, upon realization that the therapeutic bolus and dose of the therapy schedule would deliver too much drug in a given period of time, the user may have the opportunity to change the timing, amount of the therapeutic bolus, and varying doses of the therapy schedule. As one example, when a regular dose is to be delivered in close proximity to the supplemental bolus, the user may adjust the timing of the regular dose and/or reduce the amount of the regular dose, while possibly leaving other, later doses generally unchanged. Alternatively, the user may adjust the amount and/or timing of the therapeutic bolus with or without adjusting the regular dose. IMD 12 may include a clock that tracks a relative or absolute time, which may be synchronized with a clock of programmer 20. IMD 12 may utilize the clock to determine when to administer a dose according to a therapy schedule or bridging procedure, a supplemental, therapeutic bolus, a priming bolus, or other dose or bolus. In one example, IMD 12 may use the clock to determine specific times at which to administer a dose or a bolus. In another example, IMD 12 may use a timer that counts from an end of a first dose or bolus to a beginning of a subsequent dose or bolus. IMD 12 may also use a timer to count from a beginning of a dose or bolus to an end of the dose or bolus.

FIG. 14 is another example screenshot for displaying, with a device for programming an implantable fluid delivery device, a first graphical representation of a supplemental bolus to be delivered by the implantable fluid delivery device and displaying, simultaneously with the first graphical representation, a second graphical representation of programmed doses of a therapy schedule to be delivered by the implantable fluid delivery device.

Figure 15:
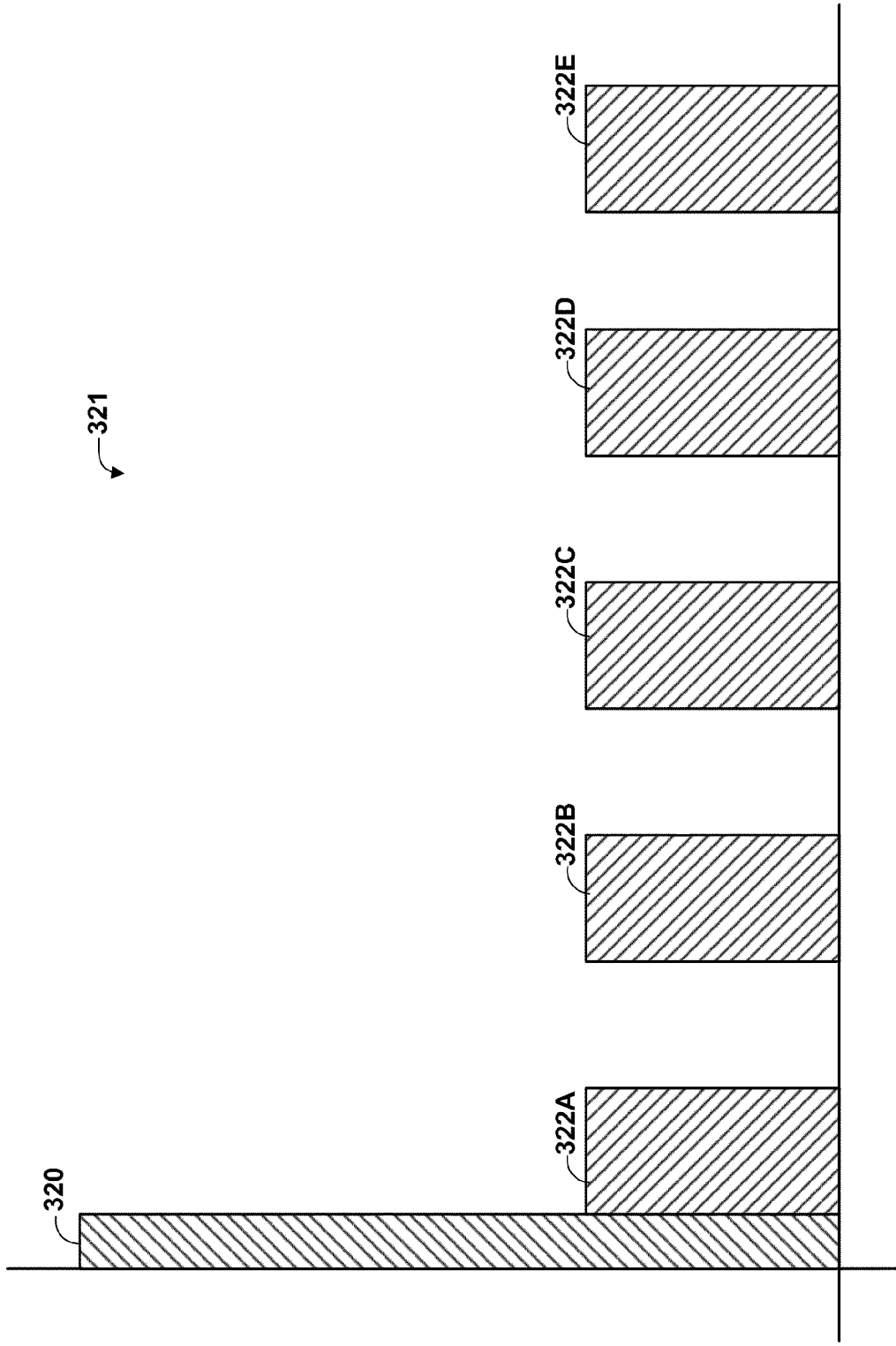
FIG. 15 is a block diagram illustrating a graph of an example dosing program for an implantable medical device that includes a therapeutic bolus representation and a series of therapy schedule dose representations.

FIG. 15 is a block diagram illustrating a graph 321 of an example dosing program for IMD 12 that includes a supplemental, therapeutic bolus representation 320 and a series of therapy schedule dose representations 322A-322E (therapy schedule dose representations 322). A graph similar to graph 321 may be presented as graph 300 of FIG. 14 in some cases.

Therapeutic bolus representation 320 corresponds to a therapeutic bolus to be delivered by IMD 12 to patient 16 in accordance with the dosing program, which may be a one-time therapeutic bolus. Therapy schedule dose representations 322 each correspond to a dose of fluid to be delivered by IMD 12 in accordance with a recurring therapy schedule of the dosing program when the dosing program is loaded onto IMD 12, e.g., after programmer 20 sends the dosing program to IMD 12 via telemetry module 88. Again, graph 321 may correspond to graph 300 of FIG. 14. That is, user interface screen 120 of FIG. 14 may display graph 321 instead of graph 300, in one example.

In the example of FIG. 15, therapeutic bolus representation 320 is immediately followed by therapy schedule dose representation 322A. Therefore, a user of programmer 20 may see that patient 16 will receive the quantity of drug corresponding to the area of both therapeutic bolus representation 320 and therapy schedule dose representation 322A. The user of programmer 20 may therefore determine whether that quantity of drug may present a risk of excessive dosage to patient 16.

When the user determines that the dosing program represented by graph 321 may cause a risk of excessive dosage to patient 16, the user may modify the dosing program, e.g., either the therapeutic bolus or the therapy schedule, to reduce the risk of excessive dosing. The user may also elect to keep patient 16 in a hospital or other facility so that the user may observe patient 16 and provide assistance to patient 16 if patient 16 begins to exhibit symptoms of excessive dosing. The user may also decide to modify the therapeutic bolus, e.g., by delivering the therapeutic bolus for less time, at a lower rate, or to cancel the therapeutic bolus altogether. For example, if a dose to be delivered according to the therapy schedule occurs in close temporal proximity after a priming phase and is at a sufficient level, the therapeutic bolus may not be necessary. The user may also decide to take other actions in response to the potential risk of excessive dosage, such as adjusting timing or amounts of one or more regular doses in the therapy schedule of the dosing program. The user may also determine that graph 321 does not present a risk of excessive dosage to patient 16 and may therefore program IMD 12 using programmer 20 according to the pending dosing program.

Figure 16:
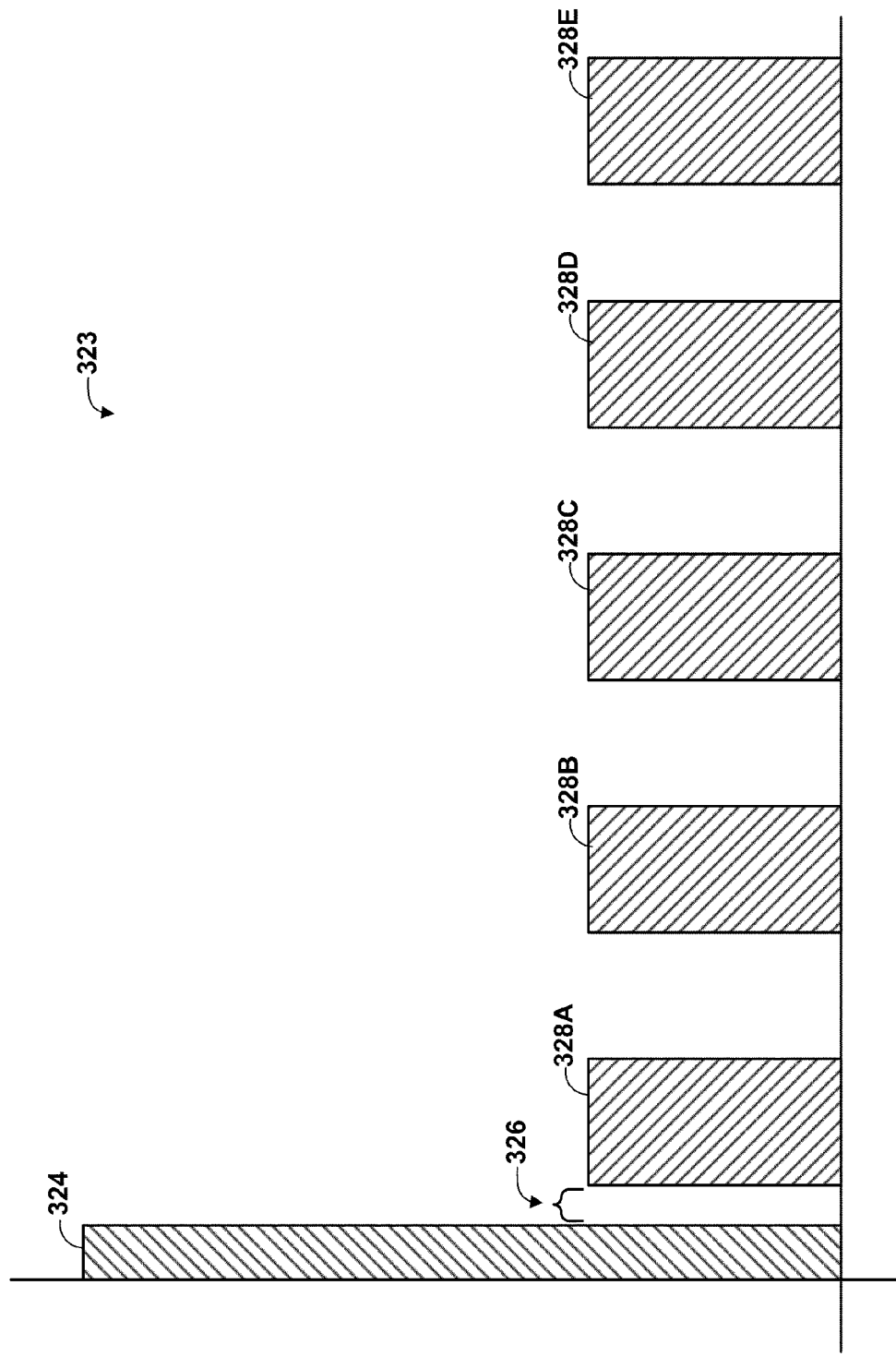
FIG. 16 is a block diagram illustrating a graph of another example dosing program for an implantable medical device that includes a therapeutic bolus representation and a series of therapy schedule dose representations.

FIG. 16 is a block diagram illustrating graph 323 of another example dosing program for IMD 12 that includes a therapeutic bolus representation 324 and a series of therapy schedule dose representations 328A-328E (therapy schedule dose representations 328). Graph 323 may correspond to graph 300 of FIG. 14. In the example of FIG. 16, therapeutic bolus representation 324 and therapy schedule dose representation 328A are separated by a slight gap 326. Although gap 326 indicates to a user of programmer 20 that IMD 12 will not administer a drug to patient 16 during the time represented by gap 326, the quantity of drug delivered to patient 16 by IMD 12 during the time represented by therapeutic bolus representation 324 may still pose an excessive dosing risk to patient 16 when IMD 12 administers the bolus corresponding to therapy schedule dose representation 328A. To facilitate timing- and amount-based analysis, the x and y axes of the graph 323 of FIG. 16 may present appropriate units, with time on the y axis and amount on the x axis. The user may therefore elect to proceed with or to modify the pending dosing program of IMD 12 before programming IMD 12 with the pending dosing program.

Figure 17:
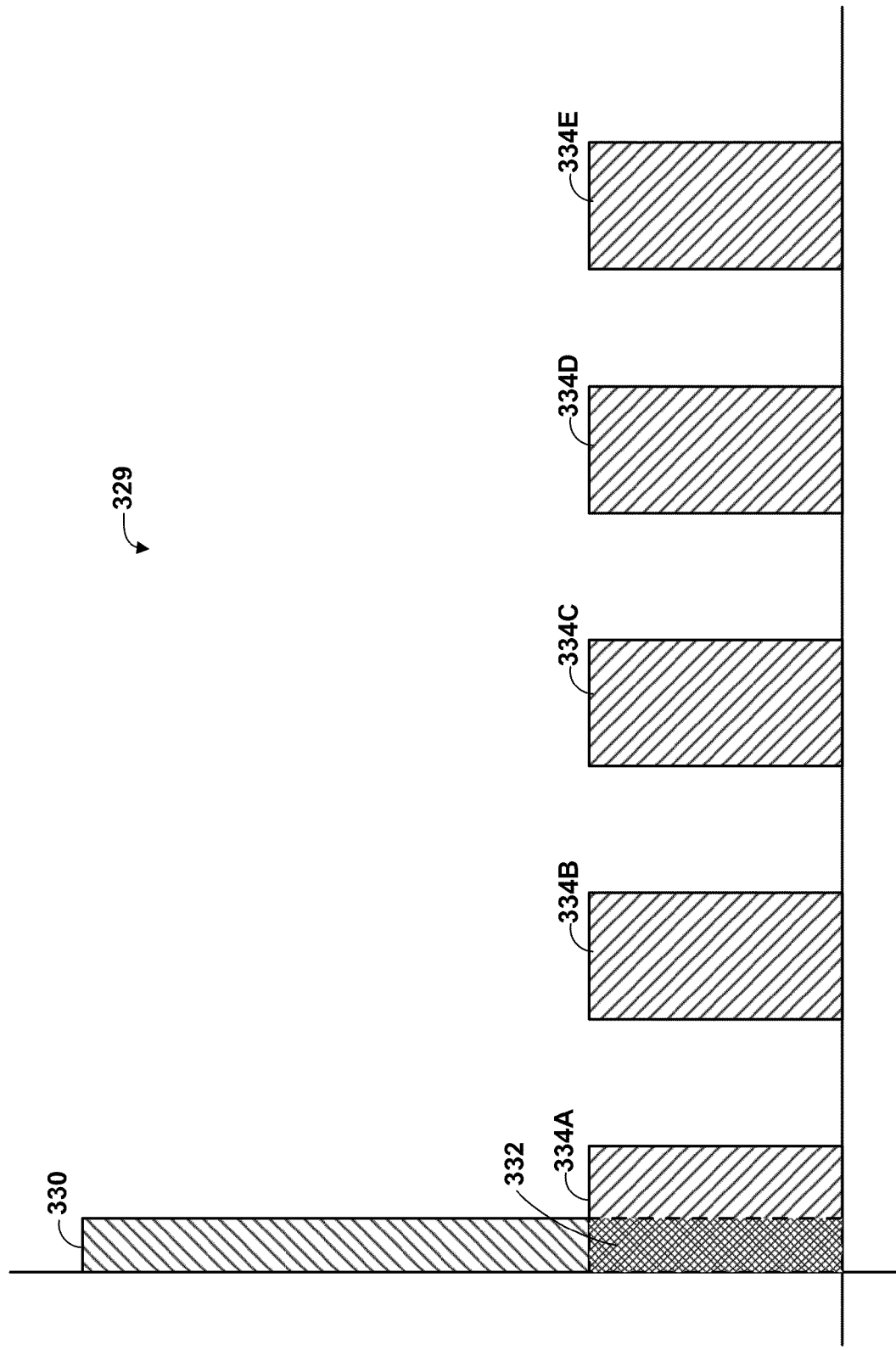
FIG. 17 is a block diagram illustrating a graph of another example dosing program for an implantable medical device that includes a therapeutic bolus representation and a series of therapy schedule dose representations.

FIG. 17 is a block diagram illustrating graph 329 of another example dosing program for IMD 12 that includes a therapeutic bolus representation 330 and a series of therapy schedule dose representations 334A-334E (therapy schedule dose representations 334). Graph 329 may correspond to graph 300 of FIG. 14. In the example of FIG. 17, therapeutic bolus representation 330 overlaps therapy schedule dose representation 334A, as indicated by overlap region 332, indicating that IMD 12 will deliver the therapeutic bolus at a time when IMD 12 is programmed to deliver a dose according to the therapy schedule of the dosing program. IMD 12 will not necessarily administer two doses of drug to patient 16 during a time corresponding to therapeutic bolus representation 330. Nevertheless, the dosing program represented by graph 329 may pose a risk of excessive dosage to patient 16. The user may visually inspect graph 329 to determine whether the pending dosing program poses a risk of excessive dosage to patient 16 when delivered in conjunction with bolus 330 of graph 329.

Figure 18:
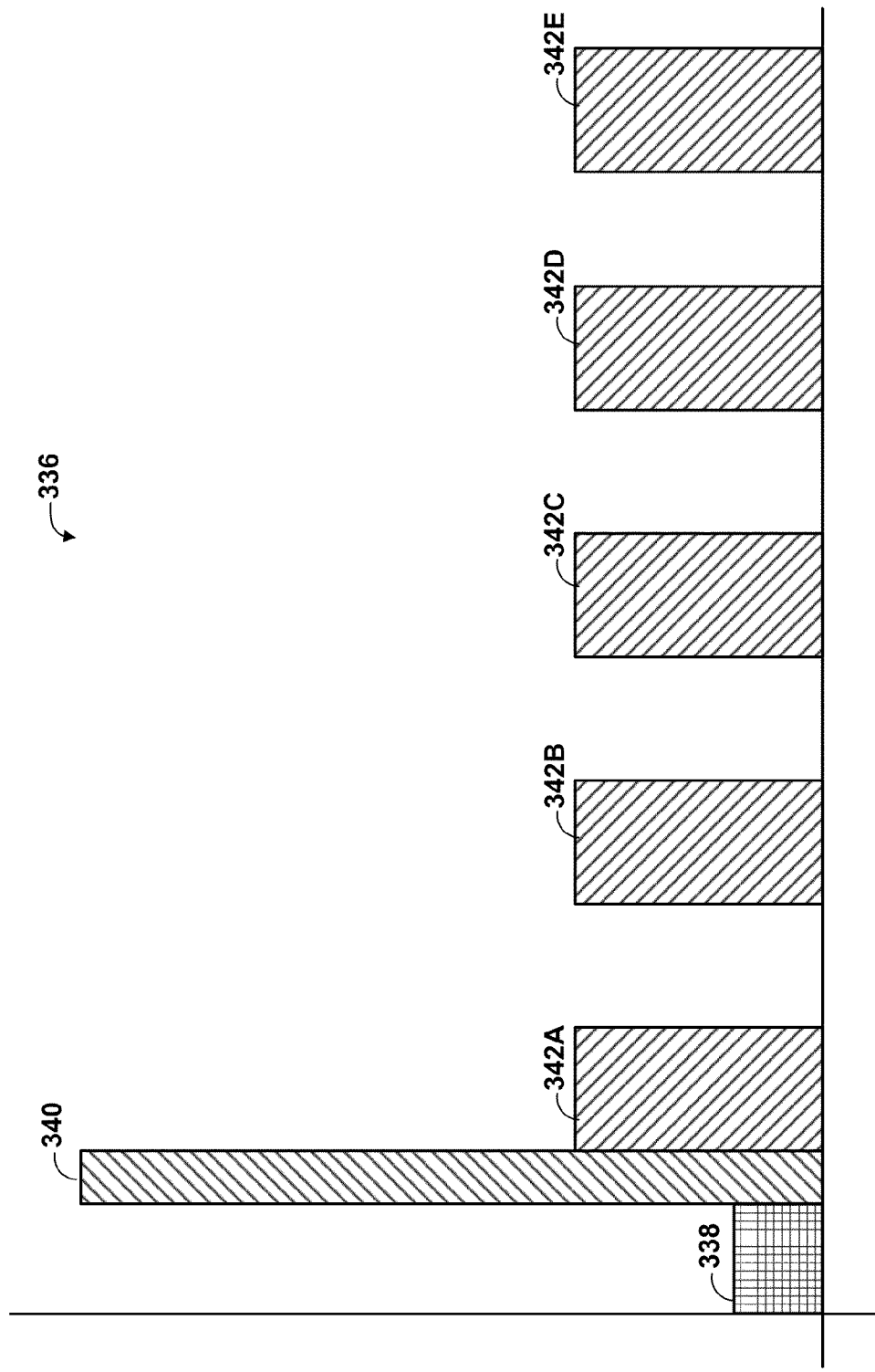
FIG. 18 is a block diagram illustrating a graph of another example dosing program for an implantable medical device that includes a priming bolus representation, a therapeutic bolus representation, and a series of therapy schedule dose representations.

FIG. 18 is a block diagram illustrating graph 336 of another example dosing program for IMD 12 that includes a priming bolus 338, a supplemental, therapeutic bolus representation 340, and a series of therapy schedule dose representations 342A-342E (therapy schedule dose representations 342). Graph 336 may correspond to graph 300 of FIG. 14. In FIG. 18, the length of priming bolus 338 is relatively short for ease of illustration. In many cases, the length of time for which priming bolus 338 is delivered may be substantially longer than the length of time for which supplemental, therapeutic bolus 340 is delivered. The example of FIG. 18 illustrates that IMD 12 may administer a therapeutic bolus following a priming bolus delivered during a priming phase of IMD 12 to move fluid containing a therapy agent to the tip of catheter 18. In other examples, IMD 12 may administer a therapeutic bolus that is not affiliated with the priming phase of IMD 12. As one example, patient 16 may have control means for causing IMD 12 to deliver a therapeutic bolus during the therapy schedule in addition to the doses delivered during the therapy schedule. IMD 12 may further include limiting means to limit a quantity of drug that IMD 12 is able to deliver to patient 16 to prevent patient 16 from causing an excessive dosage. As another example, a clinician or other user may have similar control means for causing IMD 12 to administer a therapeutic bolus. A user of programmer 20 may also program IMD 12 to administer one or more therapeutic boluses to patient 16 as part of the dosing program for IMD 12.

Figure 19:
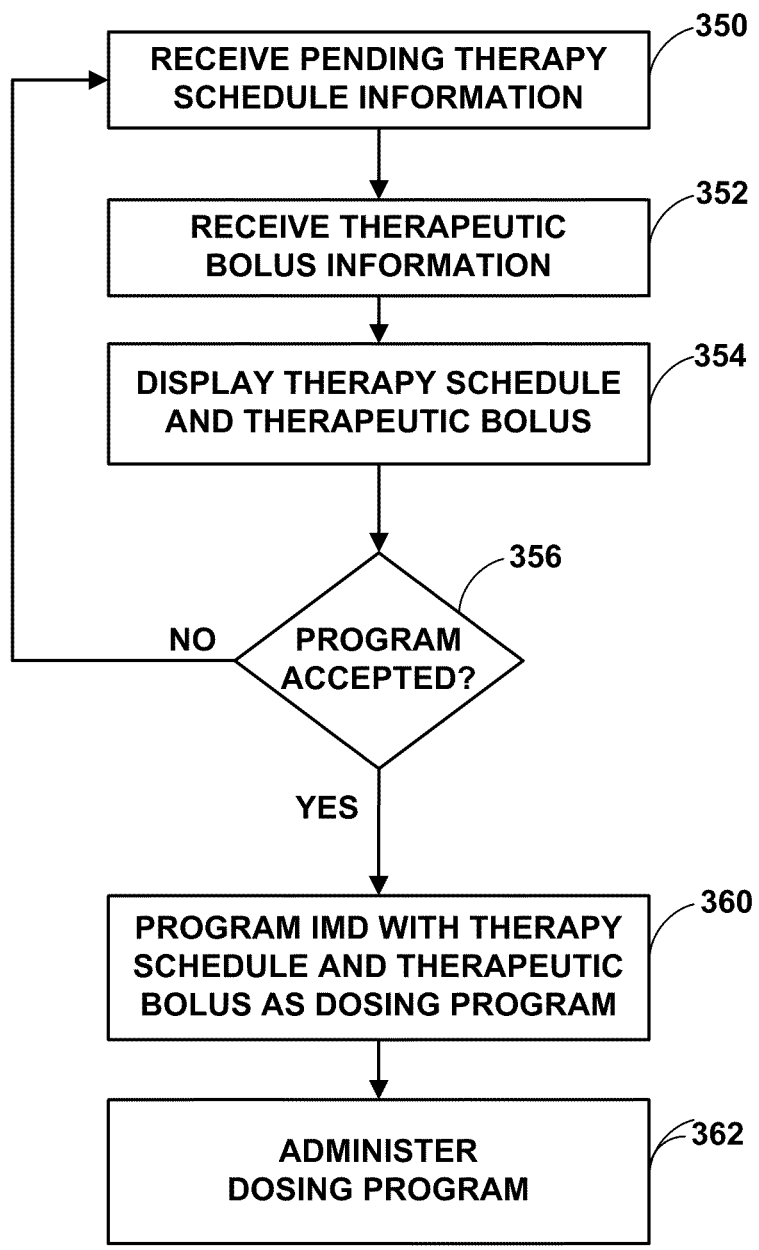
FIG. 19 is a flowchart illustrating a method for simultaneously displaying both a representation of a therapeutic bolus and a representation of a bolus of a therapy schedule with a programmer device.

FIG. 19 is a flowchart illustrating a method for simultaneously displaying both a representation of a therapeutic bolus and a representation of a dose of a therapy program with programmer 20. That is, the method of FIG. 19 is an example method for displaying, with a device for programming an implantable fluid delivery device, a first graphical representation of a supplemental bolus to be delivered by the implantable fluid delivery device and displaying, simultaneously with the first graphical representation, a second graphical representation of programmed doses of a therapy schedule to be delivered by the implantable fluid delivery device. Initially, programmer 20 receives pending therapy schedule information for a dosing program to be sent to IMD 12 (350). Programmer 20 may, for example, receive the pending therapy schedule information from a user, from a computer-readable medium that stores the pending programming information, or from another source. As one example, programmer 20 may receive the therapy schedule information using the user interface of the example of FIG. 12. The pending therapy schedule may repeat at a regular interval, such as every 24-hour time period. The pending therapy schedule may comprise one or more doses of fluid to be administered by IMD 12 at various times and for various durations.

Programmer 20 also receives therapeutic bolus information (352). The therapeutic bolus information may comprise one or more therapeutic boluses to be administered by IMD 12. The therapeutic bolus information may coincide with an event or phase of IMD 12, such as a priming phase of IMD 12. The therapeutic bolus information may cause IMD 12 to deliver a therapeutic bolus prior to a first dose of fluid to be administered according to the therapy schedule in accordance with the pending therapy schedule information.

Programmer 20 may then simultaneously display both a representation of the therapy schedule and a representation of the therapeutic bolus (354). That is, programmer 20 may display both a first graphical representation of a therapeutic bolus to be delivered by the implantable fluid delivery device, such as therapeutic bolus representation 320 (FIG. 15), and a second graphical representation of a therapy schedule of the implantable fluid delivery device configured to begin after the therapeutic bolus has been delivered, such as therapy schedule dose representations 322 (FIG. 15). Again, therapeutic bolus and supplemental bolus may be used interchangeably to refer to an additional bolus that may be delivered in relation to a priming or bridging phase.

Programmer 20 may then wait for a user to accept or modify the pending programming information and/or the therapeutic bolus information (356). The user may modify the pending programming information and/or the therapeutic bolus information, in which case programmer 20 determines that the pending programming information and the therapeutic bolus information are not accepted ("NO" branch of 356). Programmer 20 may then receive new pending programming information (350) and/or new therapeutic bolus information (352).

When the user accepts the pending programming information and the therapeutic bolus information ("YES" branch of 356), programmer 20 programs IMD 12 in accordance with the dosing program that includes the therapy schedule information and the therapeutic bolus information (360). That is, programmer 20 sends the dosing program to IMD 12 via telemetry module 88, and IMD 12 receives the information via telemetry module 74 of IMD 12.

IMD 12 may also store the pending programming information and the therapeutic bolus information in memory 40. IMD 12 and programmer 20 therefore need not remain communicatively coupled after programmer 20 has finished transmitting data to IMD 12. That is, IMD 12 may deliver fluid to patient 16 according to one or more programs stored in memory 40 of IMD 12 to begin administering the dosing program for patient 16 (362).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described herein may also be embodied in a computer-readable medium, such as a computer-readable storage medium, containing instructions. Instructions embedded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
displaying, with a device for programming an implantable fluid delivery device, a first graphical representation of a supplemental bolus to be delivered by the implantable fluid delivery device, wherein the supplemental bolus is a one-time bolus administered outside of a current therapy schedule, wherein the current therapy schedule is a pre-defined program of one or more programmed doses; and
displaying, separately and simultaneously with the first graphical representation, a second graphical representation of programmed doses of the current therapy schedule to be delivered by the implantable fluid delivery device, wherein the second graphical representation is displayed such that the second graphical representation is distinguished from the first graphical representation.

2. The method of claim 1, further comprising displaying a bar chart that represents a dosing rate along a vertical axis and time along a horizontal axis.

3. The method of claim 2,
wherein displaying a first graphical representation comprises displaying the first graphical representation on a first portion of the bar chart, and
wherein displaying a second graphical representation comprises displaying the second graphical representation on a second portion of the bar chart.

4. The method of claim 3, wherein displaying the second graphical representation on a second portion of the bar chart comprises displaying the second portion of the bar chart immediately following the first portion of the bar chart.

5. The method of claim 1, further comprising displaying a third graphical representation of a priming bolus to be delivered by the implantable fluid delivery device prior to the supplemental bolus simultaneously with the first graphical representation and the second graphical representation.

6. The method of claim 1, further comprising receiving a modification to the supplemental bolus.

7. The method of claim 1, further comprising receiving a modification to at least one of the programmed doses of the current therapy schedule.

8. The method of claim 1, further comprising sending dosing program instructions to the implantable fluid delivery device, wherein the dosing program instructions comprise instructions to deliver the supplemental bolus and instructions to deliver the programmed doses of the current therapy schedule.

9. A programmer device comprising:
   a user interface comprising a display to present a graphical representation of doses of fluid to be delivered to a patient via an implantable fluid delivery device; and
   a processor that controls the user interface to separately and simultaneously present on the display a first graphical representation of a supplemental bolus to be delivered by the implantable fluid delivery device, wherein the supplemental bolus is a one-time bolus administered outside of a current therapy schedule, wherein the current therapy schedule is a pre-defined program of one or more programmed doses, and a second graphical representation of programmed doses of the current therapy schedule of the implantable fluid delivery device, wherein at least a portion of the programmed doses of the current therapy schedule follows delivery of the supplemental bolus by the implantable fluid delivery device, wherein the second graphical representation is displayed such that the second graphical representation is distinguished from the first graphical representation.

10. The device of claim 9, wherein the user interface displays a bar chart that represents a dosing rate along a vertical axis and time along a horizontal axis.

11. The device of claim 10, wherein the user interface displays the first graphical representation on a first portion of the bar chart and the second graphical representation on a second portion of the bar chart.

12. The device of claim 11, wherein the user interface displays the second portion of the bar chart immediately following the first portion of the bar chart.

13. The device of claim 9, wherein the user interface displays a third graphical representation of a priming bolus to be administered by the implantable fluid delivery device prior to the supplemental bolus simultaneously with the first graphical representation and the second graphical representation.

14. The device of claim 9, wherein the user interface receives a modification to the supplemental bolus.

15. The device of claim 9, wherein the user interface receives a modification to at least one of the programmed doses of the current therapy schedule.

16. The device of claim 9, further comprising a telemetry module that communicates with the implantable fluid delivery device.

17. The device of claim 16, wherein the telemetry module transmits dosing program instructions to the implantable fluid delivery device, wherein the dosing program instructions comprise instructions to deliver the programmed doses of the current therapy schedule and instructions to deliver the supplemental bolus.

18. A system comprising:
   an implantable fluid delivery device that delivers fluid to a patient according to a dosing program, comprising a computer-readable medium to store the dosing program and a telemetry module; and
   a programmer device comprising:
      a user interface comprising a display to present a graphical representation of doses of fluid to be delivered to a patient via an implantable fluid delivery device; and
      a processor that controls the user interface to separately and simultaneously present on the display a first graphical representation of a supplemental bolus to be delivered by the implantable fluid delivery device, wherein the supplemental bolus is a one-time bolus administered outside of a current therapy schedule, wherein the current therapy schedule is a pre-defined program of one or more programmed doses, and a second graphical representation of programmed doses of the current therapy schedule of the implantable fluid delivery device, wherein at least a portion of the doses of the current therapy schedule follows delivery of the supplemental bolus by the implantable fluid delivery device, wherein the second graphical representation is displayed such that the second graphical representation is distinguished from the first graphical representation.

19. The system of claim 18, wherein the user interface of the programmer device displays a bar chart that represents a dosing rate along a vertical axis and time along a horizontal axis.

20. The system of claim 19, wherein the user interface of the programmer device displays the first graphical representation on a first portion of the bar chart and the second graphical representation on a second portion of the bar chart.

21. The system of claim 20, wherein the user interface of the programmer device displays the second portion of the bar chart immediately following the first portion of the bar chart.

22. The system of claim 18, wherein the user interface of the programmer device displays a third graphical representation of a priming bolus to be administered by the implantable fluid delivery device prior to the supplemental bolus.

23. The system of claim 18, wherein the user interface of the programmer device receives a modification to the supplemental bolus.

24. The system of claim 18, wherein the user interface of the programmer device receives a modification to at least one of the programmed doses of the current therapy schedule.

25. The system of claim 18, wherein the programmer device further comprises a telemetry module.

26. The system of claim 25, wherein the telemetry module of the programmer device transmits dosing program instructions to the implantable fluid delivery device, wherein the dosing program instructions comprise instructions deliver the programmed doses of the current therapy schedule and instructions to deliver the supplemental bolus.

27. A device comprising:
   means for displaying a first graphical representation of a supplemental bolus to be delivered by an implantable fluid delivery device, wherein the supplemental bolus is a one-time bolus administered outside of a current therapy schedule, wherein the current therapy schedule is a pre-defined program of one or more programmed doses; and
   means for displaying, separate and simultaneously with the first graphical representation, a second graphical representation of programmed doses of the current therapy schedule to be delivered by the implantable fluid delivery device, wherein the second graphical representation is displayed such that the second graphical representation is distinguished from the first graphical representation.

28. The device of claim 27, further comprising means for displaying a bar chart that represents a dosing rate along a vertical axis and time along a horizontal axis.

29. The device of claim 28,
   wherein the means for displaying a first graphical representation comprise means for displaying the first graphical representation on a first portion of the bar chart, and
   wherein the means for displaying a second graphical representation comprise means for displaying the second graphical representation on a second portion of the bar chart.

30. The device of claim 29, wherein the means for displaying the second graphical representation on a second portion of the bar chart comprise means for displaying the second portion of the bar chart immediately following the first portion of the bar chart.

31. The device of claim 27, further comprising means for displaying a third graphical representation of a priming bolus to be administered by the implantable fluid delivery device prior to the supplemental bolus simultaneously with the first graphical representation and the second graphical representation.

32. The device of claim 27, further comprising means for receiving a modification to the supplemental bolus.

33. The device of claim 27, further comprising means for receiving a modification to at least one of the programmed doses of the current therapy schedule.

34. The device of claim 27, further comprising means for communicating with the implantable fluid delivery device.

35. The device of claim 27, wherein the means for communicating with the implantable fluid delivery device comprise means for sending dosing program instructions to the implantable fluid delivery device, wherein the dosing program instructions comprise instructions to deliver the programmed doses of the current therapy schedule and instructions to deliver the supplemental bolus.

36. A non-transitory computer-readable storage medium comprising instructions for causing a programmable processor to:
  display first graphical representation of a supplemental bolus to be delivered by an implantable fluid delivery device, wherein the supplemental bolus is a one-time bolus administered outside of a current therapy schedule, wherein the current therapy schedule is a pre-defined program of one or more programmed doses; and
  display, separately and simultaneously with the first graphical representation, a second graphical representation of programmed doses of the current therapy schedule to be delivered by the implantable fluid delivery device, wherein the second graphical representation is displayed such that the second graphical representation is distinguished from the first graphical representation.

37. The non-transitory computer-readable storage medium of claim 36, further comprising instructions to display a third graphical representation of a priming bolus to be administered by the implantable fluid delivery device prior to the supplemental bolus simultaneously with the first graphical representation and the second graphical representation.

38. The non-transitory computer-readable storage medium of claim 36, further comprising instructions to receive a modification to the supplemental bolus.

39. The non-transitory computer-readable storage medium of claim 36, further comprising instructions to receive a modification to at least one of the programmed doses of the current therapy schedule.

40. The non-transitory computer-readable storage medium of claim 36, further comprising instructions to send dosing program instructions to the implantable fluid delivery device, wherein the dosing program instructions comprise instructions to deliver the supplemental bolus and instructions to deliver the programmed doses of the current therapy schedule.

* * * * *